(12) United States Patent
Browka et al.

(10) Patent No.: US 11,975,168 B2
(45) Date of Patent: May 7, 2024

(54) DISINFECTANT CAP

(71) Applicant: Becton, Dickinson and Company, Franklin Lakes, NJ (US)

(72) Inventors: Edward P. Browka, Sherrill, NY (US); Chang Jiang, Butler, NJ (US); Amir Harandi, Bloomingdale, NJ (US); Tom Moskal, Ringwood, NJ (US); Jiayu Liu, Bloomingdale, NJ (US); Narasinha C. Parasnis, Nanuet, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 413 days.

(21) Appl. No.: 17/080,009

(22) Filed: Oct. 26, 2020

(65) Prior Publication Data
US 2021/0146113 A1    May 20, 2021

Related U.S. Application Data

(60) Provisional application No. 63/021,867, filed on May 8, 2020, provisional application No. 62/936,878, filed on Nov. 18, 2019.

(51) Int. Cl.
*A61M 39/16*    (2006.01)
*A01N 47/44*    (2006.01)
*A61M 39/20*    (2006.01)

(52) U.S. Cl.
CPC .......... *A61M 39/162* (2013.01); *A01N 47/44* (2013.01); *A61M 39/20* (2013.01)

(58) Field of Classification Search
CPC ... A61M 39/162; A61M 39/20; A61M 39/165
See application file for complete search history.

(56) References Cited

U.S. PATENT DOCUMENTS 3,403,679 A    10/1968    Sinclair et al.
4,417,890 A    11/1983    Dennehey et al.
(Continued)

FOREIGN PATENT DOCUMENTS

CA    2803761 A1    12/2011
CA    2523133 C    2/2013
(Continued)

OTHER PUBLICATIONS

PCT International Search Report and Written Opinion in PCT/US2020/041097 dated Oct. 27, 2020, 18 pages.
(Continued)

*Primary Examiner* — Bradley J Osinski
(74) *Attorney, Agent, or Firm* — Servilla Whitney LLC

(57) ABSTRACT

A disinfection cap is described for connection to a medical connector, the disinfection cap includes a housing having a top wall and sidewall forming a cavity, disinfectant or antimicrobial agent and a ball disposed within the cavity. An outer surface of the housing includes a thread sufficient to interlock with a mating feature of a threaded connector, or more specifically a male luer connector. The cap may also include a peelable seal to prevent the disinfectant or the antimicrobial agent from exiting the cavity. The cavity of the cap may also include one or more ribs disposed on the inner surface of the cavity to retain the ball in the cavity, forming a flow channel as the ball is depressed further into the cavity. An exterior sidewall surface of the housing may include a plurality of grip members.

19 Claims, 22 Drawing Sheets

(56) References Cited

U.S. PATENT DOCUMENTS

| | | | |
|---|---|---|---|
| 4,597,758 A * | 7/1986 | Aalto | A61M 39/20 604/263 |
| 4,642,102 A | 2/1987 | Ohmori | |
| 4,711,363 A | 12/1987 | Marino | |
| 4,738,376 A | 4/1988 | Markus | |
| 4,795,432 A | 1/1989 | Karczmer | |
| 4,813,940 A | 3/1989 | Parry | |
| 4,906,231 A | 3/1990 | Young | |
| 4,950,250 A | 8/1990 | Haber et al. | |
| 5,084,017 A | 1/1992 | Maffetone | |
| 5,395,347 A | 3/1995 | Blecher et al. | |
| 5,496,288 A | 3/1996 | Sweeny | |
| 5,591,138 A | 1/1997 | Vaillancourt | |
| 5,676,406 A | 10/1997 | Simmons et al. | |
| 5,688,241 A | 11/1997 | Asbaghi | |
| 5,755,696 A | 5/1998 | Caizza | |
| 5,984,123 A | 11/1999 | Mogami et al. | |
| 5,984,899 A | 11/1999 | D'Alessio et al. | |
| RE36,885 E | 9/2000 | Blecher et al. | |
| 6,565,529 B1 | 5/2003 | Kimber et al. | |
| 6,632,199 B1 | 10/2003 | Tucker et al. | |
| 6,884,237 B2 | 4/2005 | Asbaghi | |
| 6,926,697 B2 | 8/2005 | Malenchek | |
| 7,083,605 B2 | 8/2006 | Miyahara | |
| 7,361,159 B2 | 4/2008 | Fiser et al. | |
| 7,513,888 B2 | 4/2009 | Sircom et al. | |
| 7,811,261 B2 | 10/2010 | Rubinstein et al. | |
| 8,012,131 B2 | 9/2011 | Moser et al. | |
| 8,062,265 B2 | 11/2011 | Millerd | |
| 8,162,882 B2 | 4/2012 | Rubinstein et al. | |
| 8,303,541 B2 | 11/2012 | Chun | |
| 8,333,738 B2 | 12/2012 | Millerd | |
| 8,388,894 B2 | 3/2013 | Colantonio | |
| 8,439,870 B2 | 5/2013 | Moyer et al. | |
| 8,496,627 B2 | 7/2013 | Chelak et al. | |
| 8,636,688 B2 | 1/2014 | Shaw | |
| 8,636,703 B2 | 1/2014 | Foshee et al. | |
| 8,647,307 B2 | 2/2014 | Gratwohl et al. | |
| 8,647,308 B2 | 2/2014 | Solomon et al. | |
| 8,663,129 B2 | 3/2014 | Allen et al. | |
| 8,715,231 B2 | 5/2014 | Woehr | |
| 8,721,627 B2 | 5/2014 | Alpert et al. | |
| 8,747,355 B2 | 6/2014 | Rubinstein et al. | |
| 8,777,504 B2 | 7/2014 | Shaw et al. | |
| 8,784,388 B2 | 7/2014 | Charles et al. | |
| 8,827,961 B2 | 9/2014 | Emmott et al. | |
| 8,961,475 B2 | 2/2015 | Solomon et al. | |
| 8,968,241 B2 | 3/2015 | Liversidge | |
| 8,979,794 B2 | 3/2015 | Chevallier | |
| 9,039,989 B2 | 3/2015 | Lui et al. | |
| 9,050,416 B2 | 6/2015 | Feret et al. | |
| 9,061,106 B2 | 6/2015 | Roberts et al. | |
| 9,067,024 B2 | 6/2015 | Roberts et al. | |
| 9,132,223 B1 | 9/2015 | Wakeel | |
| 9,186,466 B2 | 11/2015 | Zachek et al. | |
| 9,192,449 B2 | 11/2015 | Kerr et al. | |
| 9,352,099 B2 | 5/2016 | Roberts et al. | |
| 9,352,100 B2 | 5/2016 | Ward et al. | |
| 9,352,101 B2 | 5/2016 | Roberts et al. | |
| 9,370,327 B2 | 6/2016 | Teoh | |
| 9,399,125 B2 | 7/2016 | Burkholz | |
| 9,408,632 B2 | 8/2016 | Erskine | |
| 9,445,760 B2 | 9/2016 | Allen et al. | |
| 9,694,140 B2 | 7/2017 | Rubinstein et al. | |
| 9,848,810 B2 | 12/2017 | Allen et al. | |
| 10,099,048 B2 | 10/2018 | Chiu et al. | |
| 10,166,381 B2 | 1/2019 | Gardner et al. | |
| 10,376,686 B2 | 8/2019 | Burkholz et al. | |
| 10,589,080 B2 | 3/2020 | Hitchcock et al. | |
| 10,603,481 B2 | 3/2020 | Avula et al. | |
| 10,871,246 B2 | 12/2020 | Marici et al. | |
| 11,353,147 B2 | 6/2022 | Marici | |
| 11,511,100 B2 | 11/2022 | Ryan | |
| 11,628,288 B1 | 4/2023 | Solomon et al. | |
| 2003/0093009 A1 | 5/2003 | Newby et al. | |
| 2003/0209681 A1 | 11/2003 | Leinsing et al. | |
| 2004/0039341 A1 | 2/2004 | Ranalletta | |
| 2004/0044318 A1 | 3/2004 | Fiser et al. | |
| 2005/0147525 A1 | 7/2005 | Bousquet | |
| 2005/0197646 A1 | 9/2005 | Connell et al. | |
| 2007/0060904 A1 | 3/2007 | Vedrine et al. | |
| 2008/0010766 A1 | 1/2008 | Kaufman et al. | |
| 2008/0171995 A1 | 7/2008 | Vitullo et al. | |
| 2008/0177250 A1 | 7/2008 | Howlett et al. | |
| 2009/0008393 A1 | 1/2009 | Howlett et al. | |
| 2009/0062766 A1 | 3/2009 | Howlett et al. | |
| 2010/0000040 A1 | 1/2010 | Shaw et al. | |
| 2010/0049170 A1 | 2/2010 | Solomon et al. | |
| 2010/0050351 A1 | 3/2010 | Colantonio et al. | |
| 2010/0100056 A1 | 4/2010 | Cawthon et al. | |
| 2010/0298770 A1 | 11/2010 | Rubinstein et al. | |
| 2011/0046603 A1 | 2/2011 | Felsovalyi et al. | |
| 2011/0054440 A1 | 3/2011 | Lewis | |
| 2011/0264037 A1 | 10/2011 | Foshee et al. | |
| 2012/0039764 A1 * | 2/2012 | Solomon | A61M 25/0097 422/292 |
| 2012/0109073 A1 | 5/2012 | Anderson et al. | |
| 2012/0111368 A1 | 5/2012 | Rahimy et al. | |
| 2012/0123386 A1 | 5/2012 | Tsals | |
| 2012/0265163 A1 | 10/2012 | Cheng et al. | |
| 2012/0302997 A1 | 11/2012 | Gardner et al. | |
| 2013/0085474 A1 | 4/2013 | Charles et al. | |
| 2013/0171030 A1 | 7/2013 | Ferlic et al. | |
| 2013/0197485 A1 | 8/2013 | Gardner et al. | |
| 2013/0033864 A1 | 12/2013 | Solomon et al. | |
| 2013/0338644 A1 | 12/2013 | Solomon et al. | |
| 2014/0052074 A1 | 2/2014 | Tekeste | |
| 2014/0135706 A1 | 5/2014 | Rubinstein et al. | |
| 2014/0148781 A1 | 5/2014 | Tekeste | |
| 2014/0150832 A1 | 6/2014 | Rogers et al. | |
| 2014/0228772 A1 | 8/2014 | Ward et al. | |
| 2014/0364803 A1 | 12/2014 | Rubinstein et al. | |
| 2015/0094659 A1 | 4/2015 | Schraga | |
| 2015/0094666 A1 | 4/2015 | Bates et al. | |
| 2015/0182704 A1 | 7/2015 | Chevallier | |
| 2015/0190580 A1 | 7/2015 | Imai et al. | |
| 2015/0190586 A1 | 7/2015 | Takemoto | |
| 2015/0374968 A1 | 12/2015 | Solomon et al. | |
| 2016/0045629 A1 | 2/2016 | Gardner et al. | |
| 2016/0067422 A1 | 3/2016 | Davis et al. | |
| 2016/0158520 A1 | 6/2016 | Ma et al. | |
| 2017/0203092 A1 | 7/2017 | Ryan et al. | |
| 2018/0085568 A1 | 3/2018 | Drmanovic | |
| 2018/0200145 A1 | 7/2018 | Sanders et al. | |
| 2018/0200500 A1 | 7/2018 | Ziebol et al. | |
| 2018/0237190 A1 | 8/2018 | Iwasaki | |
| 2018/0243547 A1 | 8/2018 | Fox et al. | |
| 2018/0256879 A1 | 9/2018 | Chiu et al. | |
| 2018/0256883 A1 | 9/2018 | Follman et al. | |
| 2019/0151643 A1 | 5/2019 | Alpert | |
| 2019/0234540 A1 | 8/2019 | Marici et al. | |
| 2019/0308006 A1 | 10/2019 | Erekovcanski et al. | |
| 2019/0351212 A1 | 11/2019 | Dudar et al. | |
| 2020/0238070 A1 | 7/2020 | Ryan | |
| 2021/0100996 A1 | 4/2021 | Wijesuriya et al. | |
| 2021/0187267 A1 | 6/2021 | Jiang | |
| 2022/0273931 A1 | 9/2022 | Jiang et al. | |
| 2023/0080687 A1 | 3/2023 | Ryan | |

FOREIGN PATENT DOCUMENTS

| | | |
|---|---|---|
| CN | 1322119 A | 11/2001 |
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103079610 A | 5/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |

(56) References Cited

FOREIGN PATENT DOCUMENTS

| | | |
|---|---|---|
| DE | 202005004079 U1 | 7/2006 |
| EP | 0589379 A1 | 3/1994 |
| EP | 2606930 A1 | 6/2013 |
| EP | 2832391 B1 | 2/2015 |
| EP | 2585146 B1 | 3/2017 |
| EP | 3275490 A1 | 1/2018 |
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2012522593 A | 9/2012 |
| JP | 2013529973 A | 7/2013 |
| JP | 2015517377 A | 6/2015 |
| JP | 2016511119 A | 4/2016 |
| JP | 2016104214 A | 6/2016 |
| MX | 2013/000081 A | 3/2013 |
| MX | 349289 B | 7/2017 |
| WO | 0019878 | 4/2000 |
| WO | 200024442 A1 | 5/2000 |
| WO | 200224551 A1 | 3/2002 |
| WO | 2011066586 A1 | 6/2011 |
| WO | 2012/013587 A1 | 2/2012 |
| WO | 2013046857 A1 | 4/2013 |
| WO | 2014159346 A1 | 10/2014 |
| WO | 2015127285 A1 | 8/2015 |
| WO | 2015174953 A1 | 11/2015 |
| WO | 2017087400 A1 | 5/2017 |
| WO | 2017095373 A1 | 6/2017 |
| WO | 2016158144 A1 | 1/2018 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |
| WO | 2019212637 A1 | 11/2019 |
| WO | 2020112767 A1 | 6/2020 |

OTHER PUBLICATIONS

International Search Report in PCT/US2019/015789, dated Apr. 16, 2019, 12 pages.
Non-Final Office Action in U.S. Appl. No. 15/838,461 dated Jul. 24, 2020, 10 pages.
Non-Final Office Action in U.S. Appl. No. 16/253,683, dated Jun. 26, 2020, 9 pages.
Non-Final Office Action in U.S. Appl. No. 16/254,747, dated Aug. 20, 2020, 14 pages.
Non-Final Office Action in U.S. Appl. No. 16/378,015, dated Oct. 30, 2020, 18 pages.
Non-Final Office Action in U.S. Appl. No. 16/838,461, dated Jul. 24, 2020, 10 pages.
PCT International Search Report and Written Opinion in PCT/US2017/065956 dated Mar. 5, 2018, 14 pages.
PCT International Search Report and Written Opinion in PCT/US2019/015096 dated Mar. 21, 2019, 12 pages.
PCT International Search Report and Written Opinion in PCT/US2019/015100 dated Apr. 10, 2019, 10 pages.
PCT International Search Report and Written Opinion in PCT/US2019/026482 dated Jul. 30, 2019, 13 pages.
PCT International Search Report and Written Opinion in PCT/US2020/015535 dated May 4, 2020, 13 pages.
PCT International Search Report and Written Opinion in PCT/US2020/041311 dated Sep. 30, 2020, 16 pages.
PCT International Search Report and Written Opinion in PCT/US2020/041312 dated Oct. 19, 2020, 11 pages.
PCT International Search Report and Written Opinion in PCT/US2020/044942 dated Oct. 16, 2020, 15 pages.
PCT International Search Report and Written Opinion in PCT/US2020/044951 dated Oct. 14, 2020, 14 pages.
PCT Invitation to Pay Additional Fees in PCT/US2021/019546, dated Jun. 15, 2021, 17 pages.
"PCT International Search Report and Written Opinion in PCT/US2021/027219 dated Oct. 22, 2021, 22 pages".
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/027220 dated Jul. 21, 2021, 15 pages.
PCT Invitation to Pay Additional Fees in PCT/US2021/027219, dated Jul. 22, 2021, 15 pages.
Non-Final Office Action in U.S. Appl. No. 16/774,853 dated Feb. 1, 2022, 12 pages.
PCT International Search Report and Written Opinion in PCT/US2020/057611 dated Feb. 5, 2021, 11 pages.
Final Office Action in U.S. Appl. No. 16/253,683, dated Dec. 23, 2020, 9 pages.
Final Office Action in U.S. Appl. No. 16/254,747, dated Jan. 22, 2021, 15 pages.
Non-Final Office Action in U.S. Appl. No. 16/378,015, dated Mar. 30, 2021, 10 pages.
PCT International Search Report and Written Opinion in PCT/US2020/065229 dated Mar. 29, 2021, 12 pages.
"Non-Final Office Action in U.S. Appl. No. 17/076,102 dated Aug. 24, 2021, 10 pages".

\* cited by examiner

FIG. '14

DISINFECTANT CAP

CROSS-REFERENCE TO RELATED APPLICATIONS

This application claims priority under 35 U.S.C. § 119(e) to U.S. Provisional Application Ser. No. 62/936,878 filed Nov. 18, 2019 and U.S. Provisional Application Ser. No. 63/021,867 filed May 8, 2020, the disclosures of which are incorporated herein by reference in their entirety.

TECHNICAL FIELD

The present disclosure relates to disinfection cap devices for disinfecting corresponding medical connectors. The present disclosure generally relates to a device for disinfecting and sterilizing access ports of medical connectors having a fitting. Generally, exemplary embodiments of the present disclosure relate to the fields of threaded or interlocking fittings, including medical caps and medical disinfection caps, and in particular caps and/or disinfection caps for uses with threaded fluid connectors. Exemplary embodiments of the present disclosure relate to male disinfection cap devices for disinfecting male threaded luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hub, port, or valve upon connection to the VAD to deliver the fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

The need to protect male connectors to reduce CLABSI and PLABSI has been rising. IV gravity sets and threaded male luer connections on syringes are subject to contamination when not protected properly. Currently when IV connectors are disconnected from central lines or peripheral lines to temporarily discontinue infusion, nurses often loop the male connector to a Y-site needle-free connector or wrap the male connector in a piece of Isopropyl Alcohol ("IPA")/alcohol impregnated wipe or cloth. However such protection is very weak and does not protect the luer from touch contamination properly. Male disinfection caps have become the state of art disinfection and protection device to disinfect and create a physical barrier on male connector to prevent microbial growth.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded male connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Disinfectants typically have a threshold limit for systemic exposure for infusion into blood stream due to biotoxicity of the disinfectants at high dosage. Thus, there is a need for a disinfection device capable of blocking the lumen of open luers to facilitate the mitigation of such disinfectant ingress into connectors, thereby reducing risk of the disinfectant entering the blood stream. There is a need for a mechanism to prevent disinfectant from entering the lumen and fluid path while providing effective disinfection of the surrounding connector or fitting.

SUMMARY

A first aspect of the present disclosure relates to a cap including a housing, a ball, a disinfectant or an antimicrobial agent and a removable seal. The housing can include a top wall, an essentially cylindrical sidewall having an exterior surface and an interior surface forming a cavity, and an open bottom formed by the cylindrical sidewall with an opening to the cavity within the housing for receiving a hub of a male luer connector.

In one or more embodiments, the upper portion of the sidewall of the housing is tapered outward toward the top wall and the lower portion of the sidewall is cylindrical.

In one or more embodiments, the upper portion of the sidewall includes a slanted surface. In one or more embodiments, the slanted surface includes one or more finger grips. In one or more embodiments, the one or more finger grips are made of an elastomeric material.

In one or more embodiments, the cavity includes an inner surface having a cylindrical sidewall and a curved top wall. An outer thread or set of tabs can be included on the exterior surface of the sidewall of the housing, the outer thread being sufficient to interlock with a mating feature of the male luer connector. In one or more embodiments, the cavity can be configured to facilitate interference fit between the cavity and the mating feature of the male luer connector. In one or more embodiments, the cavity can extend essentially from an inside surface of the top wall toward the open bottom of the housing. In one or more embodiments, the cavity can extend essentially parallel to the sidewall of the housing.

In one or more embodiments, the ball can be disposed within the cavity. In one or more embodiments, the ball disposed within the cavity and the ball is configured to provide a tight seal with the inside surface of the cavity to prevent the disinfectant or the antimicrobial agent from leaking out of the cavity in an initial state, prior to the connection of a male luer connector. In one or more embodiments, the disinfectant or antimicrobial agent disinfects an outer surface and an inner surface of the male luer connector when the male luer connector is inserted into the cavity and compresses the ball. In one or more embodiments, the removable seal can be attached to the open bottom of the housing thereby forming a seal for maintaining sterility and preserving the disinfectant or an antimicrobial agent within the cavity prior to use of the cap.

In one or more embodiments, the sidewall of the housing comprises an upper portion and a lower portion. In one or more embodiments, the upper portion of the sidewall can be tapered outward and the lower portion of the sidewall can be cylindrical. In one or more embodiments, an exterior wall surface of the sidewall of the housing can include a plurality of grip members.

In one or more embodiments, when a luer or luer tip of the male luer connector is received within the inner surface of the cavity, the hub is secured within the cavity of the cap by interlocking at least a portion of the outer thread with a mating feature on the hub of the male luer connector.

In one or more embodiments, the thread can include an inclined thread pattern. In one or more embodiments, the thread can include a helical-shaped thread pattern.

In one or more embodiments, the cap can include a removable peel seal covering the opening to the cavity to seal the ball and disinfectant or antimicrobial agent within the cavity prior to use of the cap. In one or more embodiments, the ball can be composed of rubber or plastic. In one or more embodiments, a compression of the ball toward the top wall of the housing occurs upon connection of the disinfection cap to a male luer connector, whereby compression of the ball leads to the leakage of the disinfectant or antimicrobial agent within the cavity to disinfect the male luer connector.

In one or more embodiments, the disinfectant or the antimicrobial agent can be selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more specific embodiments, the disinfectant or antimicrobial agent includes at least one of chlorhexidine gluconate and chlorhexidine diacetate.

A second aspect of the present disclosure relates to a cap including a housing. In one or more embodiments, the housing can include a semi-conical top portion having a flat top wall, a sidewall including an exterior surface having a first portion having a tapered cylindrical sidewall adjacent to the semi-conical top portion and a second portion having an essentially cylindrical sidewall adjacent to the first portion. In one or more embodiments, the sidewall of the housing comprises an upper portion and a lower portion. In one or more embodiments, an exterior wall surface of the sidewall of the housing can include a plurality of grip members. In one or more embodiments, the upper portion of the sidewall can be tapered inward and the lower portion of the sidewall can be cylindrical. In one or more embodiments, the upper portion of the sidewall of the housing can include a plurality of grip members. In one or more embodiments, the plurality of grip members taper outward. In one or more embodiments, the plurality of grip members are tear-shaped.

An open bottom formed adjacent to the second portion of the sidewall with an opening to the cavity within the housing for receiving a hub of a male luer connector.

One or more embodiments of the second aspect of the present disclosure include a ball, a disinfectant or an antimicrobial agent and a removable seal. In one or more embodiments, the ball can be disposed within the cavity. In one or more embodiments, the ball is disposed within the cavity and the ball is configured to provide a tight seal with the inner surface of the cavity to prevent the disinfectant or the antimicrobial agent from leaking out of the cavity in an initial state prior to the connection of a male luer connector.

In one or more embodiments, the cavity includes an inner surface having a first portion adjacent to the open bottom having a straight cylindrical sidewall having a first diameter D1 which is smaller than the diameter of the ball to allow the ball to rest on the first portion of the inner surface of the cavity. The inner surface of cavity includes a second tapered portion disposed adjacent to the first portion, the second tapered portion having second diameter D2 that increases along the y-axis in a direction from the open bottom toward a top wall of the cavity. The inner surface of cavity includes a third portion having a straight cylindrical sidewall having a plurality of ribs protruding toward the central axis of the cavity, the third portion of the inner surface of the cavity disposed adjacent to the second portion. The third portion having Diameter D3 that is equal to or greater than the diameter of the ball such that the ball can be under radial compression by the plurality of ribs disposed on the third portion of the inner surface of the cavity. The ball is held under radial compression by the plurality of ribs to retain the ball in the third portion cavity. The inner surface of the cavity having a straight or curved top wall disposed distally from the open bottom.

In one or more embodiments, the cavity can be configured to facilitate interference fit between the cavity and the mating feature of the male luer connector. In one or more embodiments, the cavity can extend essentially from an inner surface of a top wall of the cavity toward the open bottom of the housing. In one or more embodiments, the cavity can extend essentially parallel to the sidewall of the housing.

In one or more embodiments of the second aspect of the present disclosure, the disinfectant or antimicrobial agent disinfects an outer surface and an inner surface of the male luer connector when the male luer connector is inserted into the cavity and compresses the ball.

In one or more embodiments, the removable seal can be attached to the open bottom of the housing thereby forming a seal for maintaining sterility and preserving the disinfectant or an antimicrobial agent within the cavity prior to use of the cap.

An outer thread or set of tabs is disposed on the exterior surface of the housing, the outer thread or set of tabs being sufficient to interlock with a mating feature of the male luer connector.

In one or more embodiments, when a hub of the male luer connector is received within the inner surface of the cavity, the hub is secured within the cavity of the cap by interlocking at least a portion of the outer thread with a mating feature on the hub of the male luer connector.

In one or more embodiments, the thread can include an inclined thread pattern. In one or more embodiments, the thread can include a helical-shaped thread pattern.

In one or more embodiments, the cap can include a removable peel seal covering the opening to the cavity to seal the ball and disinfectant or antimicrobial agent within the cavity prior to use of the cap. In one or more embodiments, the ball can be composed of rubber, plastic including but not limited to thermoplastic elastomer (TPE), thermoplastic polyolefin (TPO) and other elastomeric or deformable material. In one or more embodiments, a compression of the ball toward the top wall of the housing occurs upon connection to the male luer connector, whereby compression of the ball leads to the leakage of the disinfectant or antimicrobial agent within the cavity to disinfect the male luer connector.

In one or more embodiments, the disinfectant or the antimicrobial agent can be selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more specific embodiments, the disinfectant or antimicrobial agent includes at least one of chlorhexidine gluconate and chlorhexidine diacetate.

A third aspect of the present disclosure relates to a cap including a housing having a top wall, an essentially cylindrical sidewall forming a cavity, the cavity having an inner surface, a ball disposed within an indented portion of the cavity. The indented portion is positioned adjacent to a second portion of the cavity. In one or more embodiments, the indented portion and the ball form a liquid seal. In one or more embodiments, one or more channels are disposed on a surface of the second portion of the cavity. The second portion has a diameter D1, the diameter D1 being larger than a diameter of the ball. A disinfectant or antimicrobial agent is disposed within the second portion of the cavity. An open bottom is formed by the cylindrical sidewall with an opening to the cavity within said housing for receiving a hub of a male luer connector. The cavity has an inner surface with a first portion adjacent to the open bottom having a tapered sidewall, the first portion having a second diameter D2 which is smaller than the diameter of the ball, and the second diameter D2 increasing along the y-axis in a direction from the open bottom toward a top wall of the cavity.

In one or more embodiments, an outer thread being sufficient to interlock with a mating feature of said male luer connector is disposed on the outer surface of the cylindrical sidewall.

In one or more embodiments, the one or more channels are disposed on a surface of the second portion of the cavity.

A fourth aspect of the present disclosure relates to a cap including a housing having a top wall, an essentially cylindrical sidewall forming a cavity, the cavity having an inner surface, a ball and absorbent material disposed within the cavity.

A fifth aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the second cavity of the cap upon insertion of the medical connector into the cap such that the medical connector contacts the ball and the disinfectant or antimicrobial agent.

A sixth aspect of the present disclosure pertains to an assembly. The assembly comprises the cap of one or more embodiments connected to a medical connector. In one or more embodiments, the medical connector is selected from a male luer connector or other luer connector having a male fitting.

A seventh aspect of the present disclosure pertains to packaging. In one or more embodiments, the cap of one or more embodiments disclosed herein can be packaged into a strip configuration.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Figure 1:
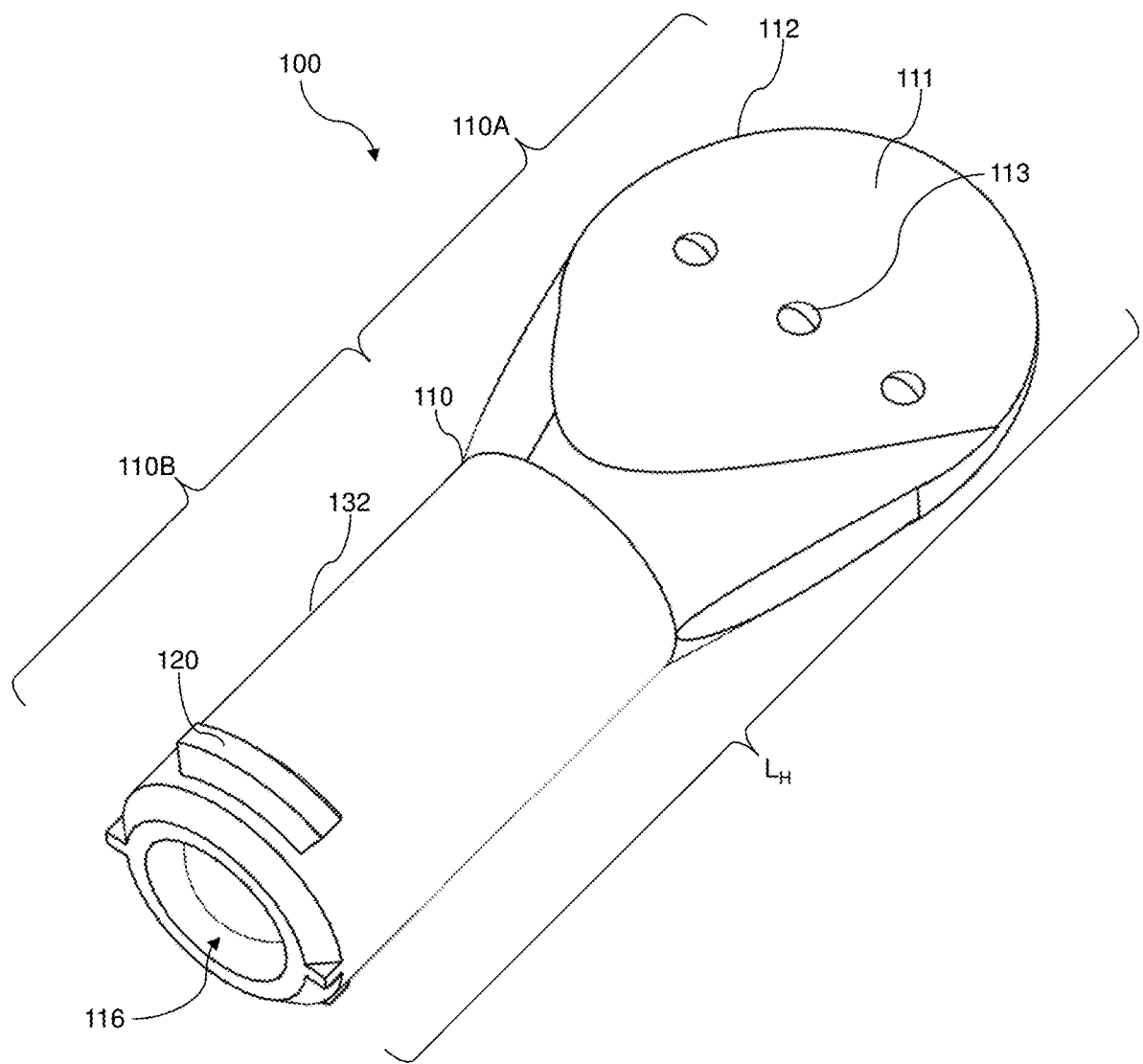
FIG. 1 illustrates a perspective view of a cap according to an exemplary first embodiment of the disclosure.

Embodiments of the disclosure pertain to a disinfection cap for connection to and disinfection of a medical connector, including threaded connectors. The connectors may be male luer connectors or a female luer connector. The disclosure aims to provide a mechanism to prevent disinfectant from entering the fluid path or a lumen of the medical connector while providing for effective disinfection for a periphery or the surrounding connector or fitting. It is contemplated that the disinfection cap disclosed herein may be utilized with male or female threaded connectors.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and male interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the male end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel.

As used herein, the term "medical device" refers to common medical devices having threaded or interlocking connections, the connections having corresponding mating elements. By way of example but not limitation, a syringe may have a male threaded connection which releasably interlocks with a secondary medical device such as a male luer connection of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "slant", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Embodiments of the cap of the present disclosure comprise a housing having a top wall defining a closed end, a sidewall having an inner surface defining a cavity, an open end formed by said cylindrical sidewall with an opening to a cavity within said housing for receiving a hub of a male luer connector, an outer thread on an exterior surface of the cylindrical sidewall that is sufficient to interlock with a mating feature of said male luer connector, a ball disposed within the cavity, and a disinfectant or antimicrobial agent, or fluid. The sidewall of the housing having a length $L_H$ extending from the closed end to an open end and defining the length of the disinfection cap. The sidewall of the cavity having a length $L_C$ extending from the top wall of the cavity disposed at the closed end of the cavity to an open end defined by the open bottom defining the length of the cavity. In one or more embodiments, the exterior surface of the housing at the open end of the disinfection cap includes a peripheral ledge extending radially outward from the open end defining an end face and an engagement surface for a peelable seal. The outer surface of the lower portion of the housing having an exterior wall surface having one or more threads adapted to engage a male luer connector, or a threaded connection or a needleless medical connection or fitting. The cap may further comprise a peelable seal and/or septum. The cap provides a mechanical barrier for connectors and contains an antimicrobial agent or fluid for disinfection. The cap of the present disclosure allows the practitioner to streamline the disinfecting process.

In particular, inserting or threading the cap onto a male connection of a medical device pushes the ball further into the cavity, thereby releasing the antimicrobial agent or fluid past the ball allowing for disinfection of the male connection, while the ball simultaneously blocks a lumen of the male connection, thus mitigating antimicrobial agent or fluid from entering the device's fluid path or lumen. The disinfectant is dispensed, bathing the periphery of the male connector.

In an exemplary implementation of the embodiments of present disclosure, a cap, connector cap or disinfection cap includes integrated threads or tabs, and other features in any and all combinations allowing it to interface with a threaded fitting of a medical device. In preferred embodiments, the cap interfaces with a male Luer fitting.

Exemplary configurations for couplers, fittings, ports and adapters may include commercially available luer locks, luer slip ports, locking ports, threaded connections, interlocking connection or generally other common medical device fitting known in the art.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Figure 2:
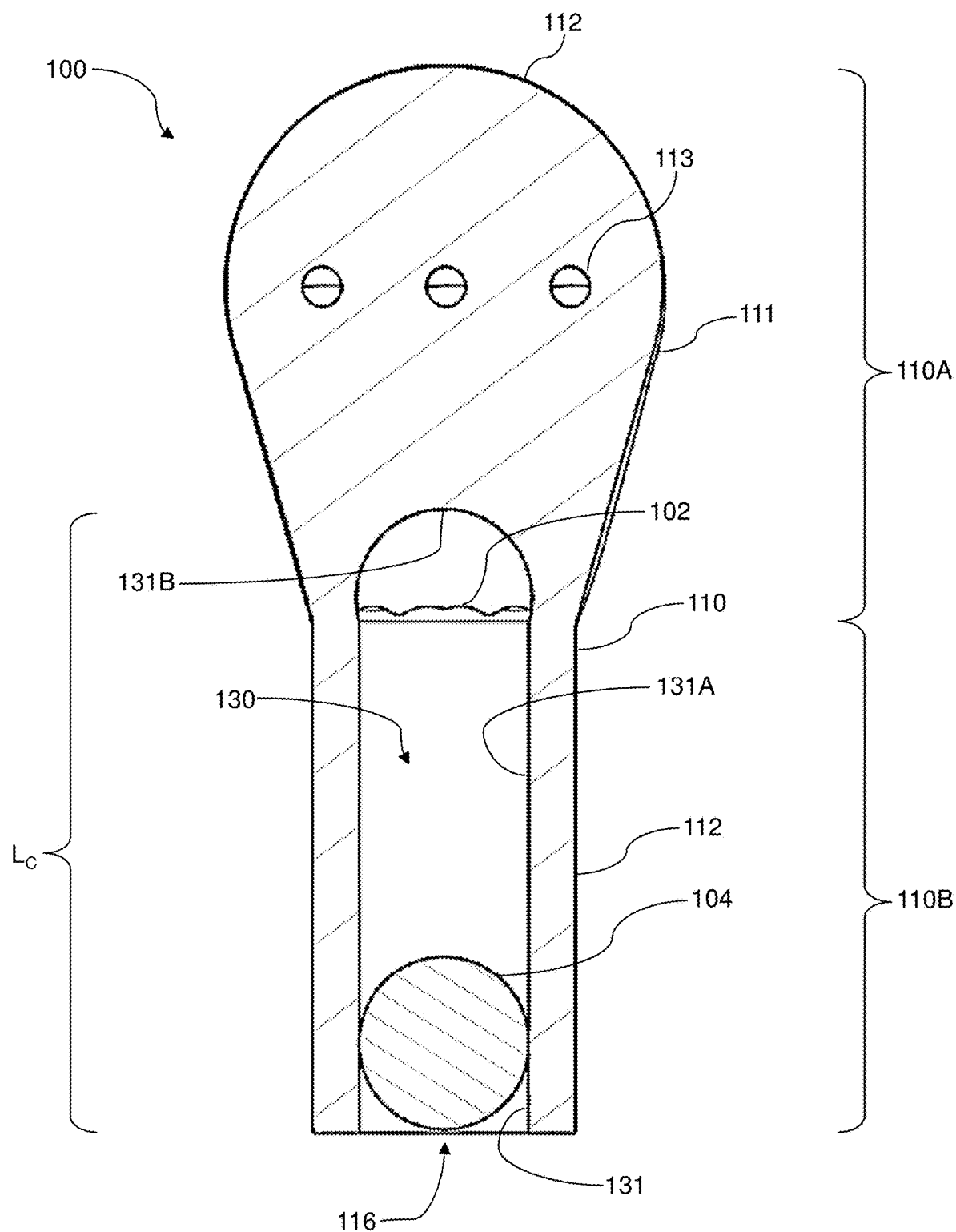
FIG. 2 illustrates a cross-sectional view of a cap according to an exemplary first embodiment of the disclosure.

As shown in FIGS. 1 and 2, a first aspect of the present disclosure relates to a disinfection cap 100 including housing 110 having an upper portion 110A and a lower portion 110B. The upper portion 110A including a top wall 112. As shown in FIG. 1, upper portion 110A may include a finger rest 111 or tab to assist in holding and rotating the cap 100 to either engage or disengage the cap 100 from the corresponding mating element on the exterior surface of the male luer connector. The finger rest 111 provides a gripping surface for the user to grasp the cap during use. The finger rest 111 may have any shape sufficient to provide a gripping surface for the user to grasp the cap during use. In one or more embodiments, one or more surfaces of finger rest 111 having a plurality of grip members 113. In one or more embodiments, there two finger rests 111 on opposing ends of the upper portion 110A of the housing for turning the cap 100. In one or more embodiments, as shown in FIG. 1, the finger rest 111 includes a contoured surface including tapers and slanting surfaces. In one or more embodiments, the contoured surface may include one or more grip members 113 on the surface of the finger rest 111 to improve grip. The one or more grip members 113 may be textured and may made of an elastomeric material. In one or more embodiments, bumps may also be present on the finger rest to indicate where to the user may grip the device to engage or disengage the cap from the male luer connector. In one or more embodiments, finger rest 111 has a gently convex or concave surface. In one or more embodiments, finger rest 111 has surface texture to improve friction with the thumb of a user.

In one or more embodiments, the lower portion 110B of the sidewall may be cylindrical. As shown in FIGS. 1 and 2, the upper portion 110A of the housing has an outwardly tapered sidewall and the lower portion 110B of the housing including an essentially cylindrical sidewall 132. In one or more embodiments, the cavity can be configured to facilitate an interference fit between the cavity and the mating feature of the male luer connector. In further embodiments, the cavity can be configured to facilitate a loose fit between the cavity and the mating feature of the male luer connector, wherein the cap 100 is secured by an outer thread or set of tabs included on the outer surface of the housing. In one or more embodiments, the inner surface of the lower portion 110B of the housing defines a cavity 130 having open bottom 116 formed by the cylindrical sidewall 132 for receiving a hub of a male luer connector. In one embodiment, cavity 130 is integrally formed with the housing 110. Cavity 130 includes an inner surface 131. In one or more embodiments, the cavity 130 includes an inner surface 131 having a cylindrical sidewall 131A and a curved top wall 131B. In one or more embodiments, the cavity 130 can extend essentially from an inner surface of the top wall toward the open bottom 116 of the housing 110. In one or more embodiments, the cavity 130 can extend essentially parallel to the sidewall 114 of the housing 110.

The outer thread or set of tabs can be included on the outer surface of the housing, the outer thread being sufficient to interlock with a mating feature of the male luer connector. In one or more embodiments, when a hub of the male luer connector is received within the inner surface of the cavity 130, the hub is secured within the cavity 130 of the cap 100 by interlocking at least a portion of the outer thread 120 with a mating feature on the hub of the male luer connector. In one or more embodiments, the exterior surface of the housing 110 of the cap 100 of the present disclosure includes outer thread 120 that has a size and pitch to engage a threadable element or segment of a male connector, such as for example, a male luer connector. In one or more embodiments, the thread 120 can include an inclined thread pattern. In one or more embodiments, the thread 120 can include a helical-shaped thread pattern. Such connectors are generally and commonly used as catheter and other fluid-tight protective connectors in medical applications. In some embodiments, cap 100 provides a protective cover for a male luer connector when engaged with the connector when threads from the male luer connector engage and form a releasable connection with threads 120 of cap 100. In one or more embodiments, as shown in FIG. 1, thread 120 can be included on the exterior surface 31 of sidewall 114 of the housing 110, the thread 120 being sufficient to interlock with a mating feature or element of the male luer connector. According to still further exemplary implementations of the embodiments of the present disclosure, male threads disposed on the exterior surface of the sidewall of the housing are sized and have a thread pattern that will engage with a standard ISO-2 type of male fitting.

One or more aspects of the present disclosure include a ball 104, a disinfectant or an antimicrobial agent 102 and a removable seal 122. In one or more embodiments, the ball 104 can be disposed within the cavity 130. In one or more embodiments, the ball 104 is configured to provide a tight seal with the inner surface 131 of the cavity 130 to prevent the disinfectant or the antimicrobial agent 102 from leaking out of the cavity 130 in an initial state prior to the connection of a male luer connector. In the preferred embodiment the ball 104 can be compressible and may be a thermoplastic elastomer ("TPE"), thermoplastic olefin ("TPO"), or an elastomer or deformable material. In other embodiments, the ball 104 may be of a rigid or hard plastic causing the housing 110 to deform. In further embodiments, the ball 110 may be glass, ceramic, metal or a composite material.

In one or more embodiments, the disinfectant or antimicrobial agent 102 disinfects an outer surface or periphery the male luer connector when the male luer connector is inserted into the cavity 130 and pushes the ball in a distal direction. In the preferred embodiment, the insertion compresses the ball 104. When inserted further into the cavity 100, the ball 104 forms an interference fit with an inner wall of the cavity 130 of the cap 100. In one or more embodiments, the ball 104 is soft and can form a slight clearance with inner sidewall 131 of the cavity 130 when subject to pressure.

Inserting or threading the cap 100 onto the threaded male connection causes the ball 104 to be further pushed into the cavity 130, thereby releasing the antimicrobial agent or fluid past the ball, allowing for disinfection of the male connection. The disinfectant is dispensed, bathing the periphery of the male connector. The ball 104 simultaneously blocks a lumen of the male connection, thus mitigating antimicrobial agent or fluid from entering the device's fluid path or lumen.

The seal created between the ball 104 and the lumen of the male connection is aided by ball deformation.

Figure 3:
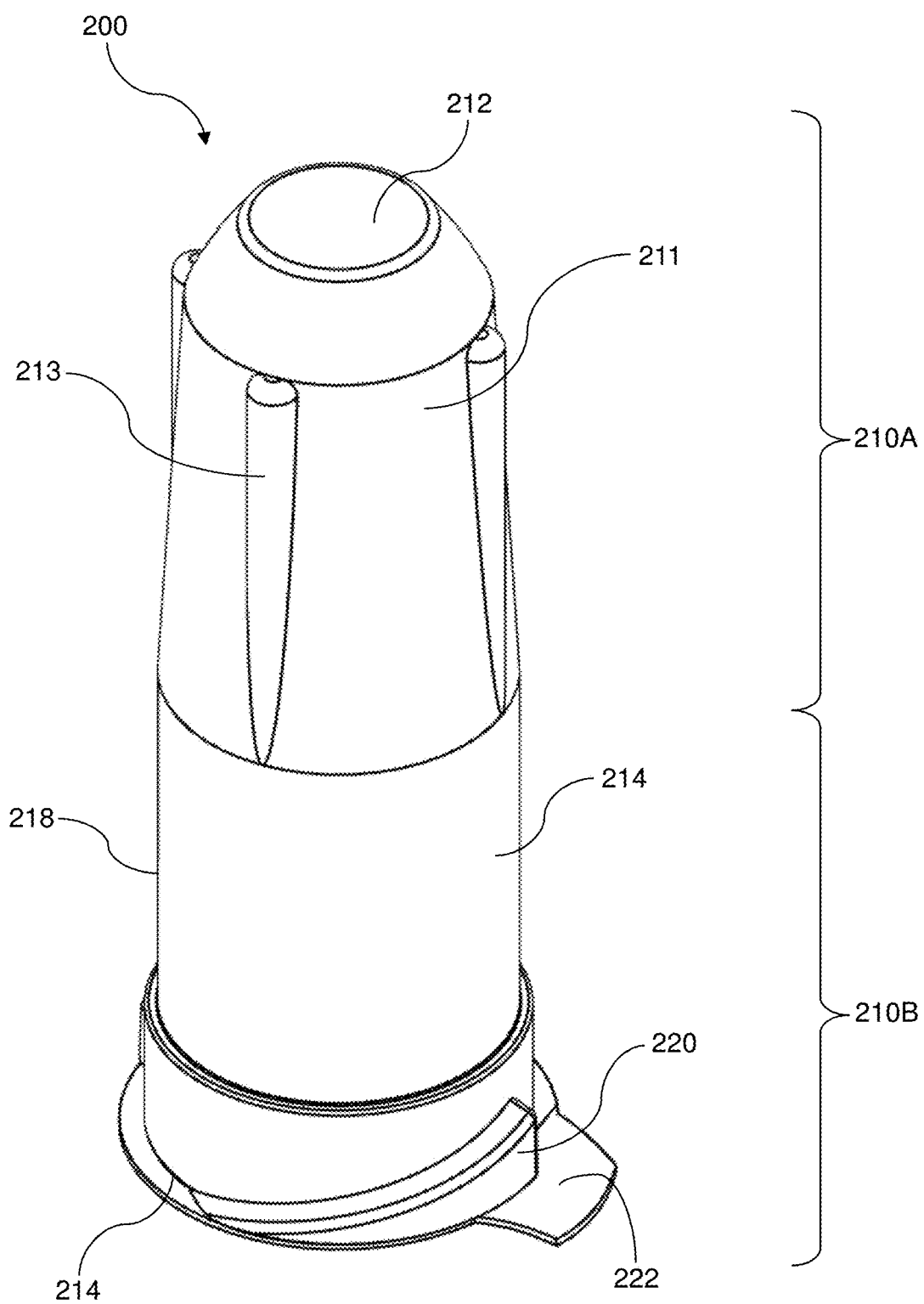
FIG. 3 illustrates a perspective view of a cap according to an exemplary second embodiment of the disclosure.
Figure 4:
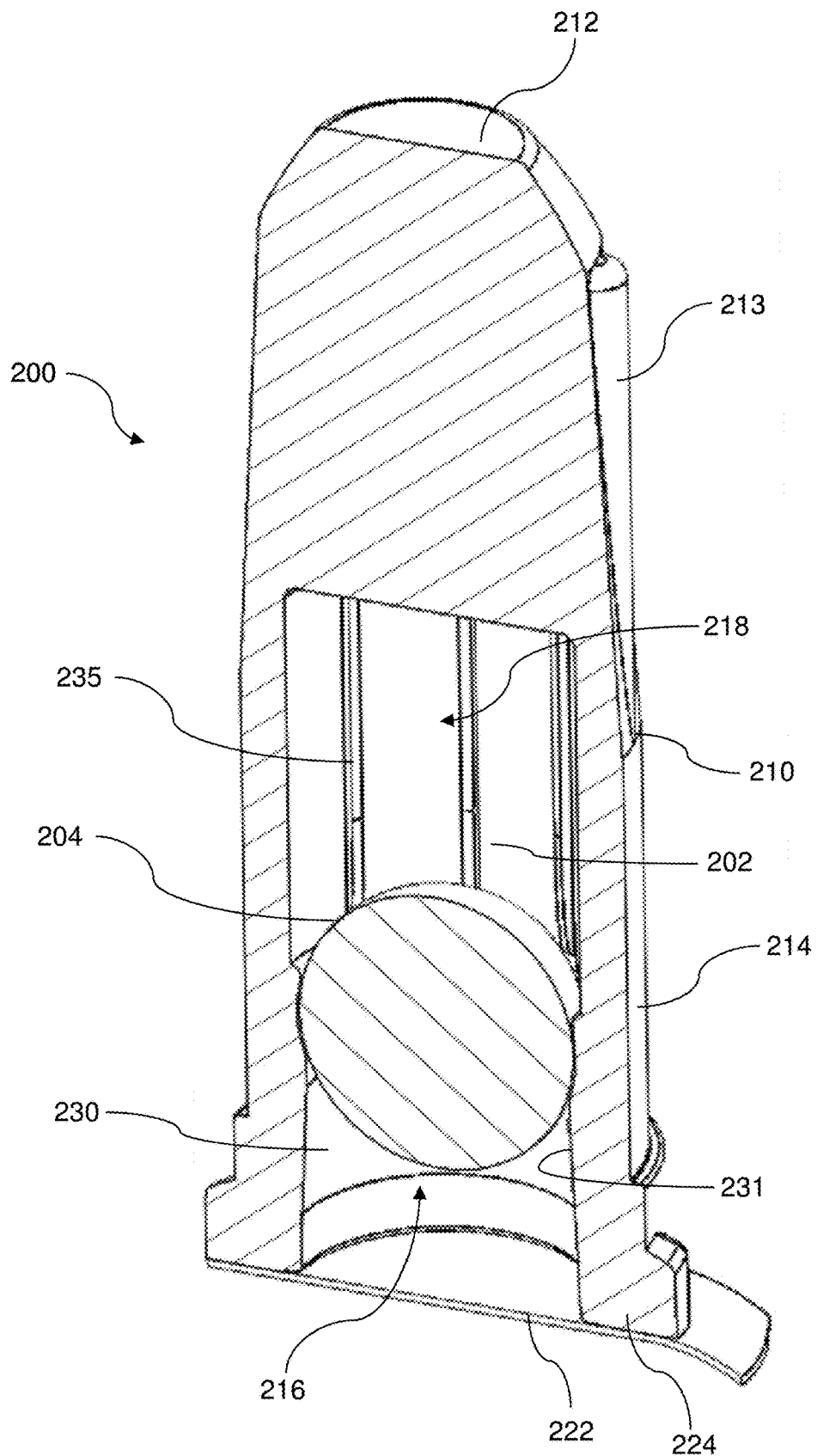
FIG. 4 illustrates a cross-sectional view of a cap according to an exemplary second embodiment of the disclosure.

As shown in FIGS. 3 and 4, a second aspect of the present disclosure relates to a cap 200 including a housing 210. In one or more embodiments, the sidewall 214 of the housing 210 comprises an upper portion 210A and a lower portion 210B. As shown in FIGS. 3 and 4, in one or more embodiments, the upper portion 210A of the sidewall can be tapered inward and the lower portion 210B of the sidewall can be cylindrical. In one or more embodiments, as shown in FIGS. 3 and 4, the upper portion 210A of housing 210 can include a semi-conical top portion having a flat top wall 212, a tapered cylindrical sidewall adjacent to the semi-conical top portion and a lower portion 210B having an essentially cylindrical sidewall. In one or more embodiments, the upper portion 210A of the sidewall of the housing can include a plurality of grip members 213. In one or more embodiments, the plurality of grip members 213 taper outward. In one or more embodiments, the plurality of grip members 213 are tear-shaped. An open bottom 216 at the proximal end of the housing having an opening to the cavity 330 within the housing 210 for receiving a hub of a male luer connector.

In one or more embodiments, the cavity 230 can be configured to facilitate interference fit between the cavity 230 and the mating feature of the male luer connector. In one or more embodiments, the cavity 230 can extend essentially from an inner surface of a top wall of the cavity toward the open bottom of the housing. In one or more embodiments, the cavity can extend essentially parallel to the sidewall of the housing.

One or more embodiments of the second aspect of the present disclosure includes a ball 204, a disinfectant or an antimicrobial agent 202 and a removable seal 222. In one or more embodiments, the ball 204 can be disposed within the cavity 230 and the ball 204 is configured to provide a tight seal with the inner surface 231 of the cavity 230 to prevent the disinfectant or the antimicrobial agent 202 from leaking out of the cavity 230 in an initial state prior to the connection of a male luer connector. Inserting or threading the cap 200 onto the threaded male connection causes the ball 204 to be further pushed into the cavity 230, thereby releasing the antimicrobial agent or fluid past the ball, allowing for disinfection of the male connection. The disinfectant is dispensed, bathing the periphery of the male connector. The ball 204 simultaneously blocks a lumen of the male connection, thus mitigating antimicrobial agent or fluid from entering the device's fluid path or lumen. The seal created between the ball 204 and the lumen of the male connection is aided by ball deformation. Thus, the intended function of the cap 200 and ball 204 is to contain the fluid, mitigate disinfectant ingress into the fluid path or lumen of the medical device and pressure seal or hold pressure in the fluid path after attachment to prevent fluid leakage when there is positive pressure in the line caused by skipping clamping the line.

In one or more embodiments, the cavity 230 includes an inner surface 230 having a first portion adjacent to the open bottom 216 having a straight cylindrical sidewall having a first diameter D1 which is smaller than the diameter of the ball 204 to allow the ball 204 to rest on the first portion of the inner surface of the cavity. The inner surface of cavity 231 includes a second tapered portion disposed adjacent to the first portion, the second tapered portion having second diameter D2 that increases along the y-axis in a direction from the open bottom 216 toward the top wall of the cavity. The inner surface of cavity 231 includes a third portion having a straight cylindrical sidewall having a plurality of ribs 235 protruding toward the central axis of the cavity, the third portion of the inner surface of the cavity disposed adjacent to the second portion. The third portion having diameter D3 that is equal to or greater than the diameter of the ball 204 such that the ball 204 can be under radial compression by the plurality of ribs 235 disposed on the third portion of the inner surface of the cavity. The ball 204 may be placed under radial compression by the plurality of ribs 235, helping in retention of the ball 204 in the third portion cavity. The inner surface of the cavity 231 having a straight or curved top wall disposed distally from the open bottom 216. In the preferred embodiment, the cavity 230 and plurality of ribs 235 have a greater rigidity than the ball 204, thus when the ball 204 is pushed further into the cavity 230, the ball 204 compressed and deforms, allowing for fluid to flow in between gaps created by the plurality of ribs 235. In further embodiments, the cavity 230 and plurality of ribs 235 may have less rigidity than the ball 204, compressing the cavity 230 and the plurality of ribs 235 as the ball 204 is pushed further into the cavity 230, where fluid flows flow in between gaps created by the plurality of ribs 235. The plurality of ribs 235 and the cavity 230 may, but not necessarily, have the same rigidity.

Referring to FIG. 3-4, rim 224 of an open bottom 216 of housing 210 may include a peripheral ledge extending radially outward from the annular sidewall at the open bottom defining an end face. The surface of the peripheral edge also defines an engagement surface where a peelable seal may be secured. In one or more embodiments, the cap can include a removable peel seal 222 covering the opening to the cavity 230 to seal the ball 204 and disinfectant or antimicrobial agent 202 within the cavity 230 prior to use of the cap 200.

Referring to FIGS. 3 and 4, in one or more embodiments, the peelable seal 222 is disposed on the engagement surface of open bottom 216 of housing 210 to prevent the disinfectant or the antimicrobial agent 202 from exiting the cavity 230 and thereby also forming a seal for maintaining sterility and preserving the disinfectant or an antimicrobial agent within the cavity 230 prior to use of the cap. The peelable seal 222 minimizes entry of potential particulate hazard and also provides a substantially impermeable enclosure for the cap 200, provides a leak prevention and protection enclosure, protects the contents of the cavity 230, and/or maintains a sealed, sterilized environment. The peelable seal 222 provides a sufficient seal at a range of temperatures, pressures, and humidity levels.

As shown in FIGS. 1-6, cavity (130, 230, 330) can include a closed distal end comprising a distal wall, an open proximal end, a sidewall extending proximally from the distal wall toward the open proximal end.

A thread or set of tabs (120, 220, 320) is disposed on the exterior surface of the housing (110, 210, 310), the thread or set of tabs (120, 220, 320) being sufficient to interlock with a mating feature of the male luer connector.

In one or more embodiments, the cap (100, 200, 300) of the present disclosure has thread or set of tabs (120, 220, 320) that have a size and pitch to engage a threadable segment of a corresponding male connector, such as for example, a male luer connector. Such connectors are generally and commonly used as catheter and other fluid-tight protective connectors in medical applications. In some embodiments, cap (100, 200, 300) provides a protective cover for a male luer connector. In one or more embodiments, the thread can include an inclined thread pattern. In one or more embodiments, the thread can include a helical-shaped thread pattern.

In one or more embodiments, when a hub of the male luer connector is received within the inner surface of the cavity, for example after a peel seal is removed or when the peal seal is pierced, the hub is secured within the cavity of the cap by interlocking at least a portion of the threads or set of tabs (120, 220, 320) of cap (100, 200, 300) with a mating feature on the hub of the male luer connector.

In one or more embodiments of the second aspect of the present disclosure, the ball 204 forms an interference fit with inner wall of the cavity 230 of the cap 200. In one or more embodiments, the ball 204 can be under radial compression by the plurality of ribs 235 on the inner surface of the cavity 230 to retain the ball 204 in the cavity 230.

Figure 5:
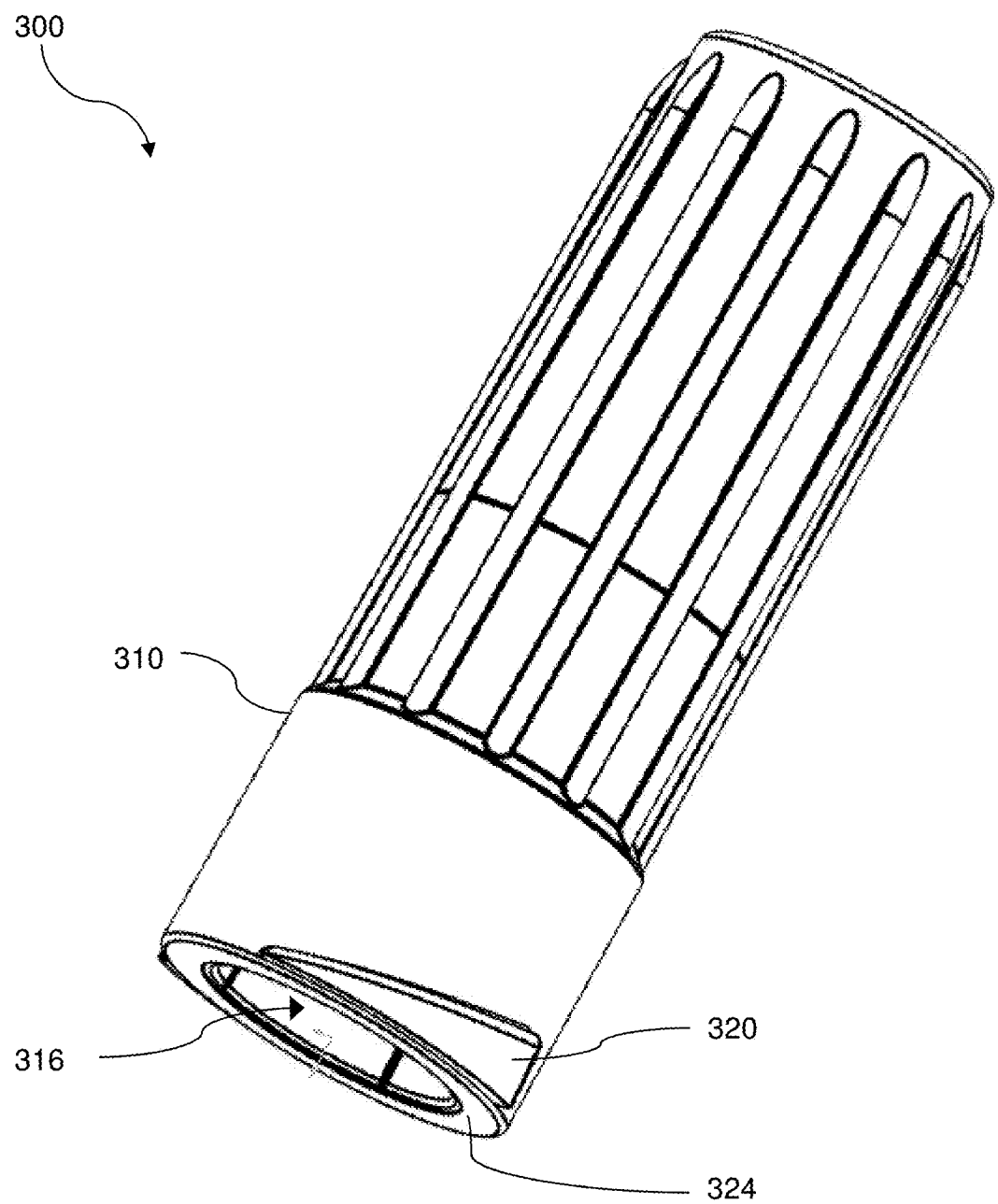
FIG. 5 illustrates a perspective view of a cap according to an exemplary third embodiment of the disclosure.
Figure 6:
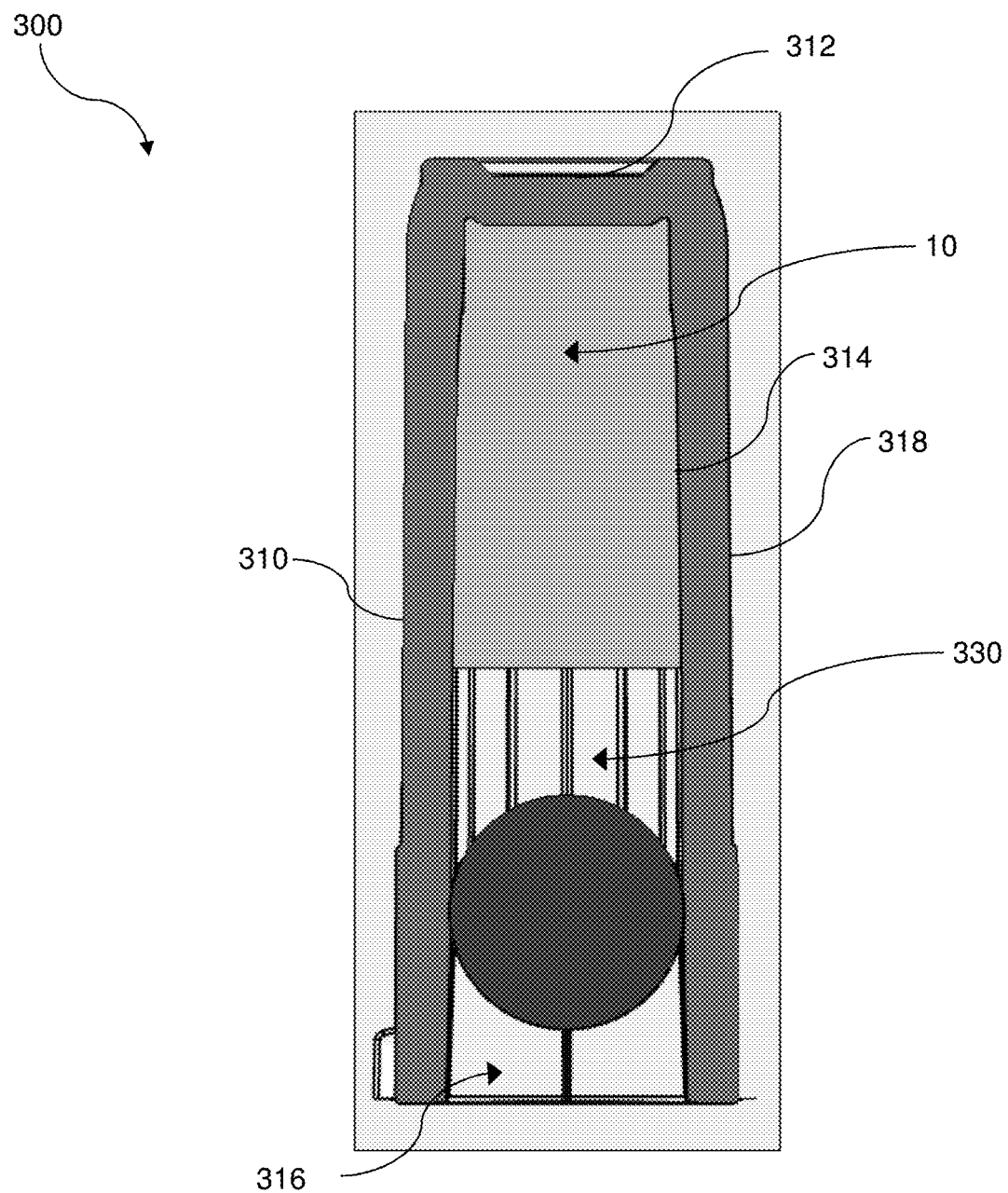
FIG. 6 illustrates a cross-sectional view of the cap according to an exemplary third embodiment of the disclosure.

A third aspect of the present disclosure relates to a sterile cap 300, as shown in FIGS. 5 and 6, a housing 310 comprises a top wall 312, an essentially cylindrical sidewall 314 forming a cavity 330, and an open bottom 316 formed by the cylindrical sidewall 304 with an opening to the cavity 330 within the housing 310 for receiving a hub of a connector of a medical device. The connector of the medical device may be a threaded connection, a needless connection, or in the preferred embodiment, a male luer connector. In one or more embodiments, the cavity includes a closed distal end comprising a distal wall, an open proximal end, and a sidewall extending proximally from the distal wall toward the open proximal end. In one or more embodiments, a thread 320 is disposed on the outer surface 318 of the housing 310, the thread 320 being sufficient to interlock with a mating feature of the male luer connector. In one or more embodiments, the thread may be formed as at least two tabs which may interlock with a twist-to-lock mating feature of the connector of the medical device. In further embodiments, the thread may be inclined or helical in shape, corresponding with the mating feature of the connector of the medical device intended to be sterilized A peelable seal 322 (not shown) may be in the form of a film and be provided to seal the open bottom 316 prior to use of the sterile cap 300, by way of example, by attachment to a surface of a rim 324 of the open bottom 316, The rim 324 may comprise a peripheral ledge extending radially outward from the sidewall 314 at the open bottom 316 defining an end face. The surface of rim 324 also defines an engagement surface where the sterile cap 300 may engage a mating surface of the male luer connector.

In one or more embodiments, the peelable seal 322 is disposed on the engagement surface of the rim 324 to prevent the disinfectant or the antimicrobial agent from exiting the cavity 330. The peelable seal 322 minimizes entry of potential particulate hazard and also provides a substantially impermeable enclosure for the cap 300, provides a leak prevention and protection enclosure, protects the contents contained within the cavity 330, and/or maintains a sealed, sterilized environment. The peelable seal 322 provides a sufficient seal at a range of temperatures, pressures, and humidity levels. In one or more embodiments, the peelable seal 322 comprises an aluminum or multi-layer polymer film peel back top. In further embodiments, the peelable seal 322 is heat-sealed or induction sealed to the end face of the locking lid or to the cap open end. In one or more embodiments, the peelable seal 322 comprises a moisture barrier. The sterile cap 300 may achieve disinfection when used on common luer connectors by integrating disinfectant or antimicrobial agent or fluid 302 in the cavity 330 of the housing 310.

In one or more embodiments, the cylindrical sidewall 314 defining the cavity may be tapered from the open bottom 316 towards the top wall 312. In an alternative embodiment, the cylindrical sidewall 314 may include a plurality of parallel portions, the plurality of parallel portions varying in diameter. In one or more embodiments, the cylindrical sidewall 314 may include a plurality of parallel portions and a plurality of tapered portions, the plurality of parallel portions and the plurality of tapered portions varying in diameter As shown in FIG. 5, in one or more embodiments, the sidewall 314 of the housing 310 comprises an upper portion 310A and a lower portion 310B. As shown in FIG. 5, in one or more embodiments, the upper portion 310A of the sidewall 310 may have a smaller diameter than the diameter of the bottom portion 310B. In one or more embodiments, as shown in FIG. 5, the upper portion 310A of housing 310 can include a tapered top portion having a top wall 312. In one or more embodiments, the upper portion 310A of the sidewall of the housing can include a plurality of grip members 313. In one or more embodiments, the plurality of grip members 313 taper outward.

Figure 7:
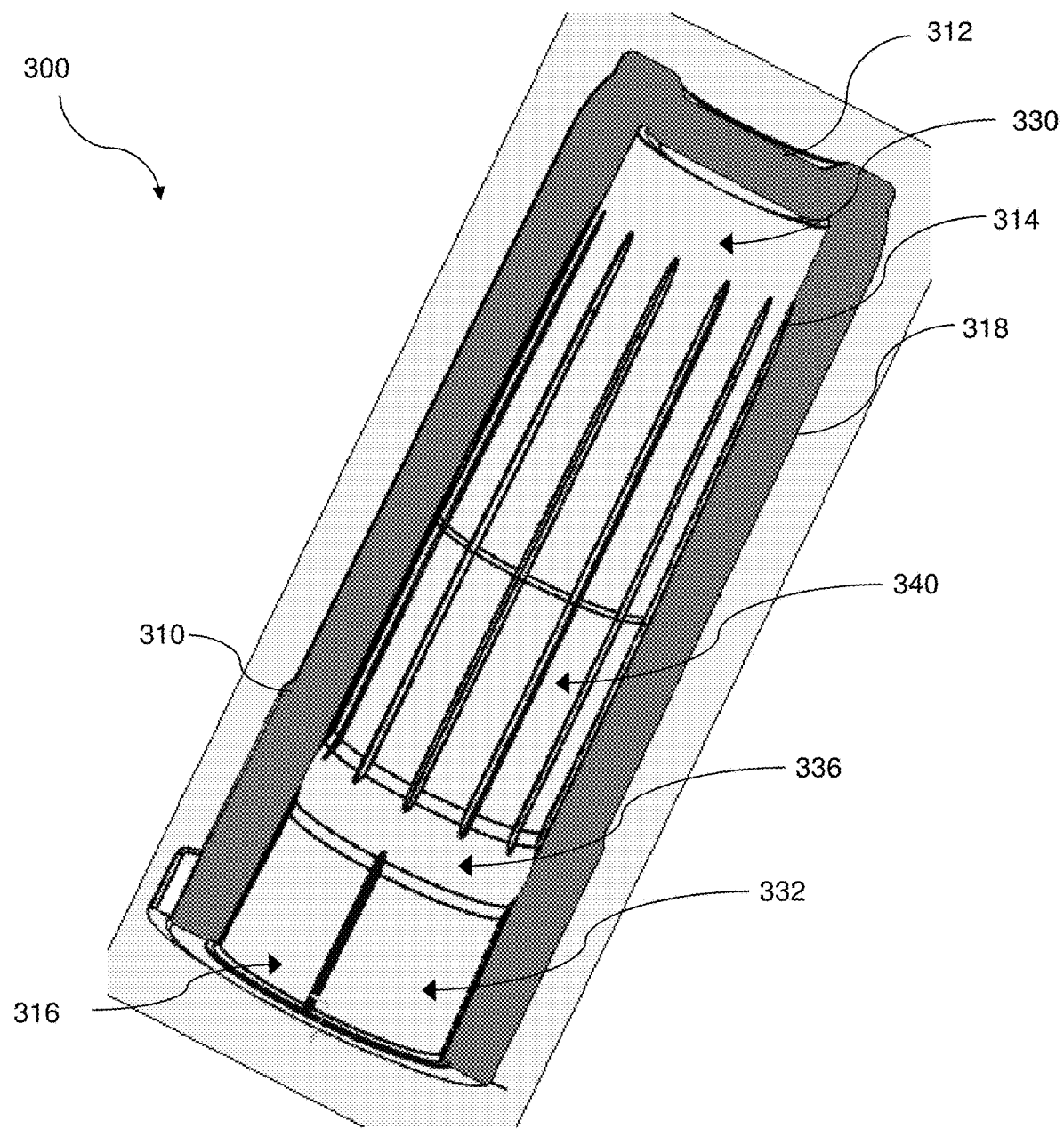
FIG. 7 illustrates a perspective cross-sectional view of the cap according to an exemplary third embodiment of the disclosure.
Figure 8:
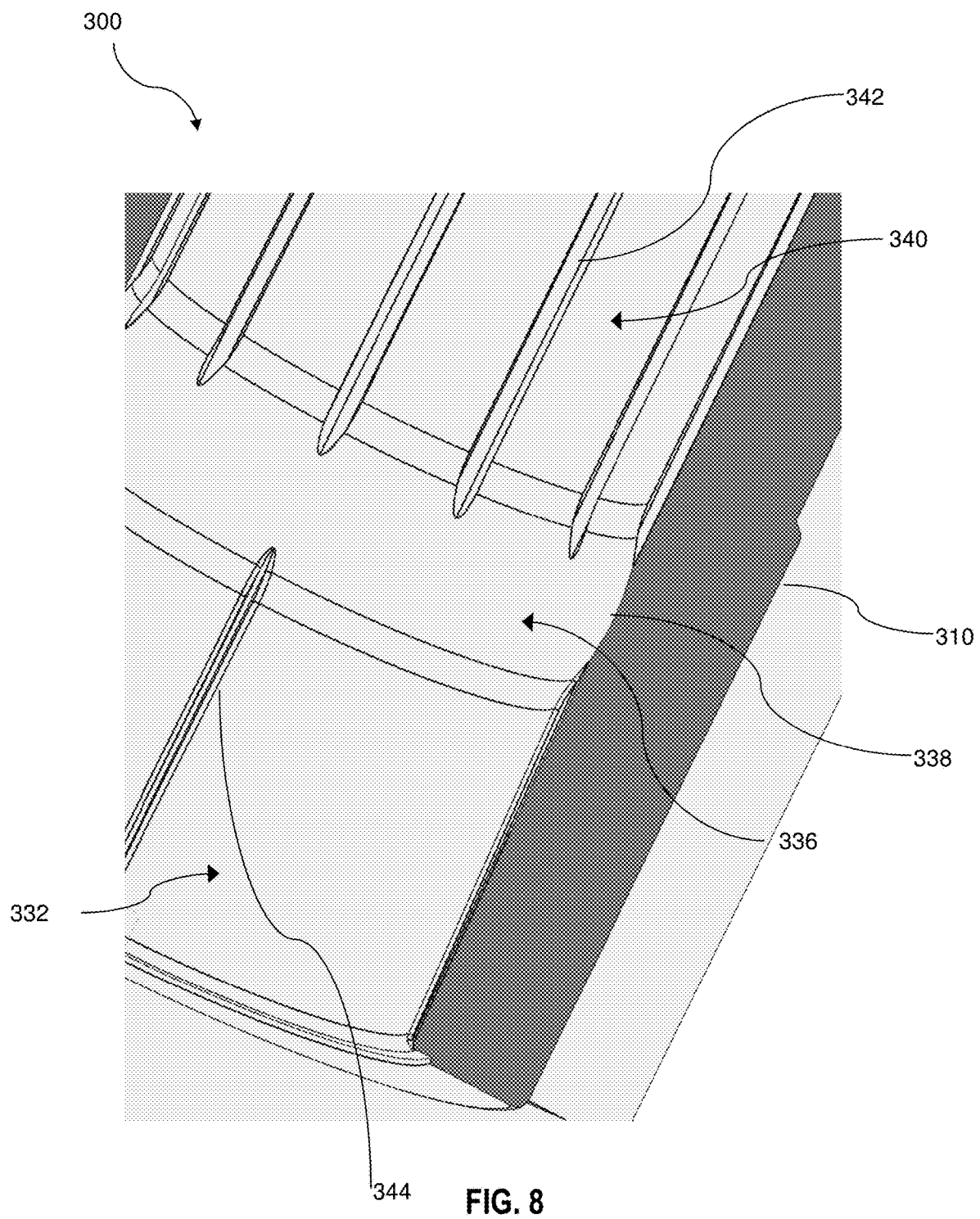
FIG. 8 illustrates a detailed perspective cross-sectional view of a cavity of the cap according to an exemplary third embodiment of the disclosure.
Figure 9:
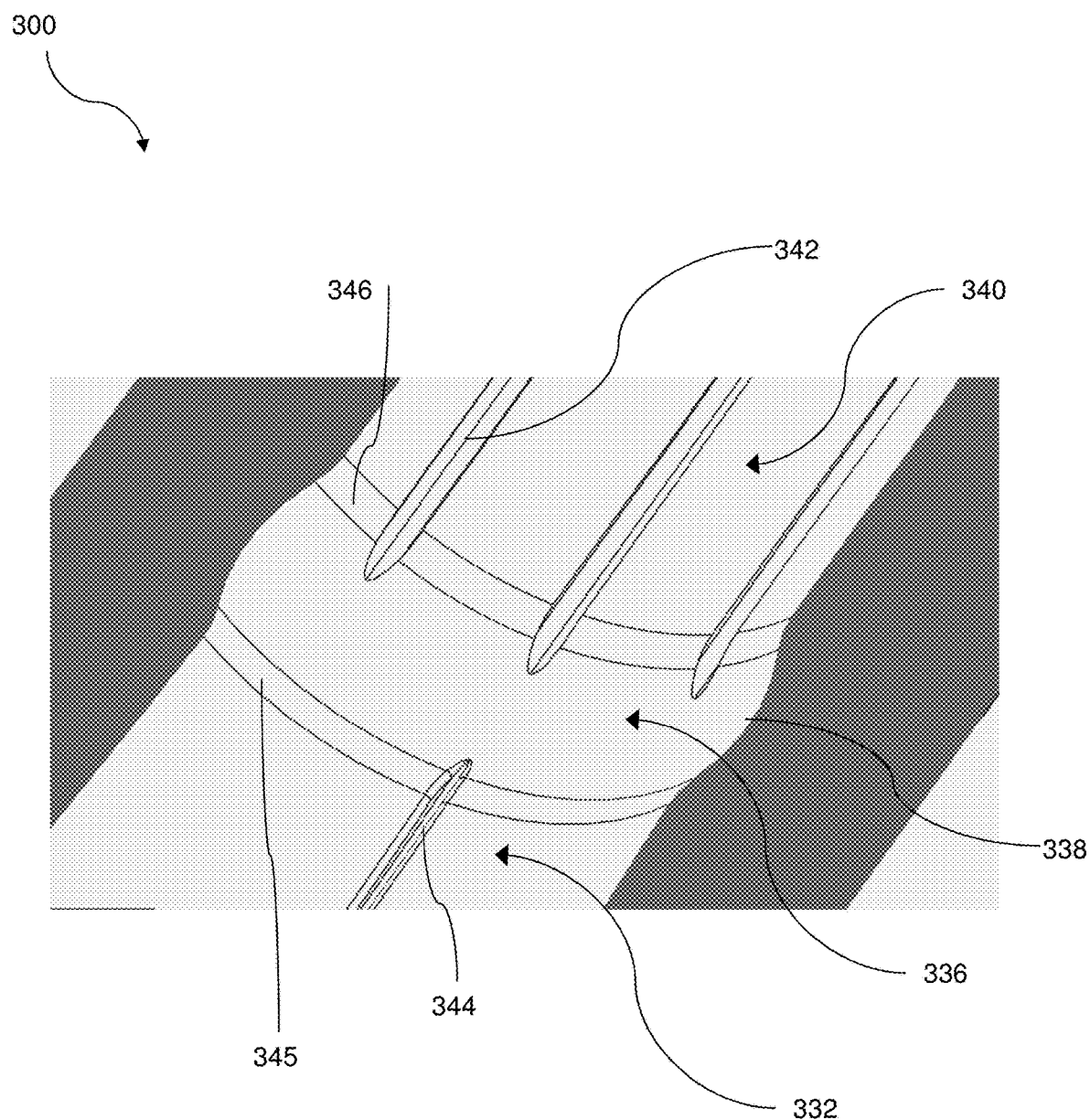
FIG. 9 illustrates yet another detailed perspective cross-sectional view of a cavity of the cap according to an exemplary third embodiment of the disclosure.

Referring to FIGS. 7-9, the cylindrical sidewall 314 includes a first cylindrical portion 332, an indented portion 336 and a second cylindrical portion 340. A proximal end of the first cylindrical portion 332 is situated adjacent to the open bottom 316. A distal end of the first cylindrical portion is disposed adjacent to a proximal end of the indented portion 336. A proximal end of the second cylindrical portion 340 is disposed adjacent to a distal end of the indented portion 336. In some embodiments, chamfered or rounded transitions may be disposed at the transitions from the first cylindrical portion 332 to the indented portion 336, and from the indented portion 338 to the second cylindrical portion 340. As depicted in FIG. 9, a proximal chamfer 344 is disposed between the first cylindrical portion 332 and indented portion 336, and a distal chamfer 346 is disposed between the indented portion 336 and the second cylindrical portion 340.

As depicted in FIG. 6, a ball 304 sits in the indented portion 336. The indented portion 336 is defined by an arc 338 extending from the proximal chamfer 334 to the distal chamfer 336. The arc diameter of the arc 338 is less than or equal to the diameter of the ball 304, the arc 338 and the ball 304 being in an interference fit, the interference fit preventing any fluid or gas communication between the first cylindrical portion 332 and the second cylindrical portion 340.

The first cylindrical portion 332 is defined by a tapered shape. The proximal diameter of the first cylindrical portion 332 is greater than or equal to the diameter of the ball 304. The distal diameter of the first cylindrical portion 332 is approximately equal to the diameter of the ball 304. Specifically, the distal diameter of the first cylindrical portion 332 is configured to prevent the ball 304 from inadvertently escaping the indented portion 336. The proximal diameter of the first cylindrical portion 332 is often, but not necessarily, configured to create interference fit with a stem of a luer or needleless connection.

The second cylindrical portion 340 is defined by a proximal section 348 and a distal section 350. The proximal section 348 has a diameter less than the diameter of the ball 304. The proximal section 348 allows for the ball 304 to restrictedly travel through the proximal section 348 in a distal direction, the ball 304 and the proximal section 348 being in an interference fit. The distal section 350 having a diameter less than the diameter of ball 304, preventing the ball 304 from traveling further in a distal direction. Alternatively, the distal section 350 may be tapered as to prevent the compressed ball 304 from traveling further in the distal direction.

The proximal section 348 of the second cylindrical portion 340 may further include a plurality of top flow channels 352 in which fluid flows through as the ball 304 is pushed within the proximal section 348. The plurality of flow channels extend radially into the housing 310. The plurality of top flow channels 352 extend from the distal chamfer 346 to the distal section 350, the proximal and distal ends of the plurality of top flow channels 352 being tapered. The first cylindrical portion 332 may further include a plurality of bottom flow channels 352 in which fluid flows through as the ball 304 is pushed within the proximal section 348 of the second cylindrical portion 340. When the ball 304 sits within the indented portion 336, fluid or gas cannot flow from the plurality of top flow channels 342 to the plurality of bottom flow channels 344, as the ball 304 is in an interference fit with the indented portion 336. The plurality of bottom flow channels 344 is intended to promote disinfectant or antimicrobial agent permeation towards the mating surface of the male luer connector. Compression of the ball 304 toward the top wall 312 of housing 310 upon connection to the male luer connector allows the connector to contact the disinfectant or antimicrobial agent to disinfect the male luer connector.

Figure 10A:
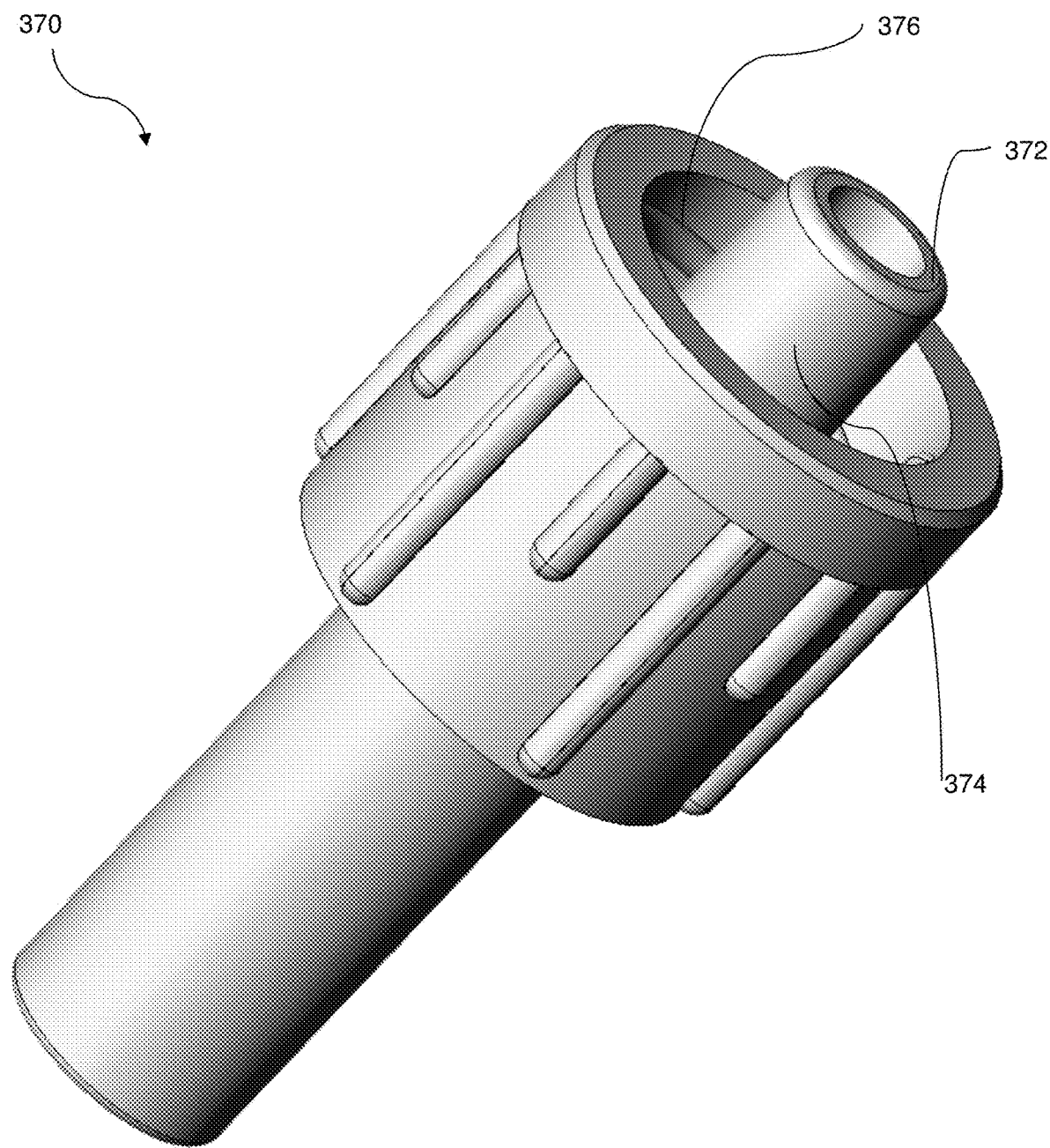
FIG. 10A illustrates a perspective view of a connector according to an exemplary third embodiment of the disclosure.
Figure 10B:
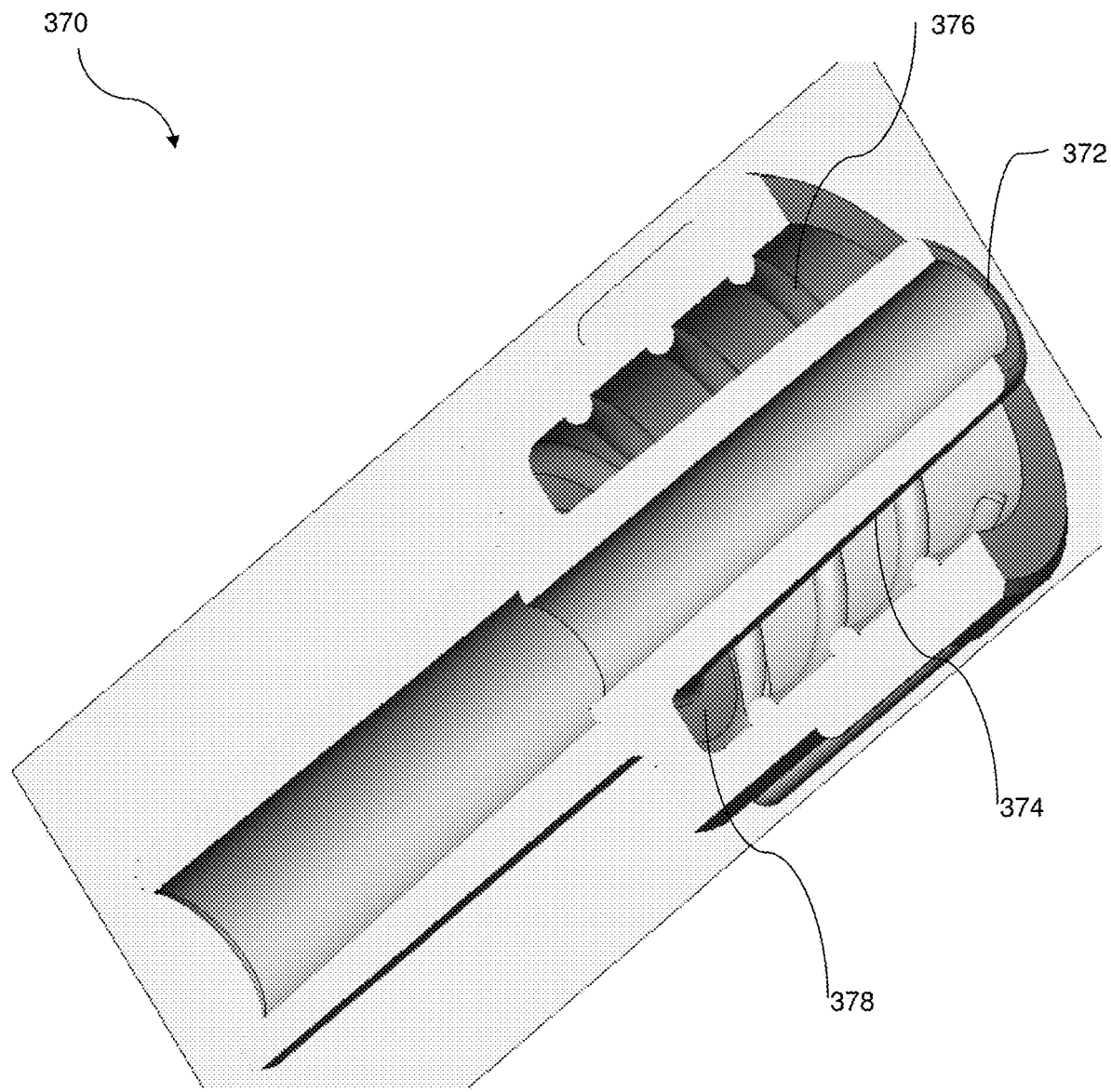
FIG. 10B illustrates a detailed perspective cross-sectional view of connector cap according to an exemplary third embodiment of the disclosure.
Figure 11A:
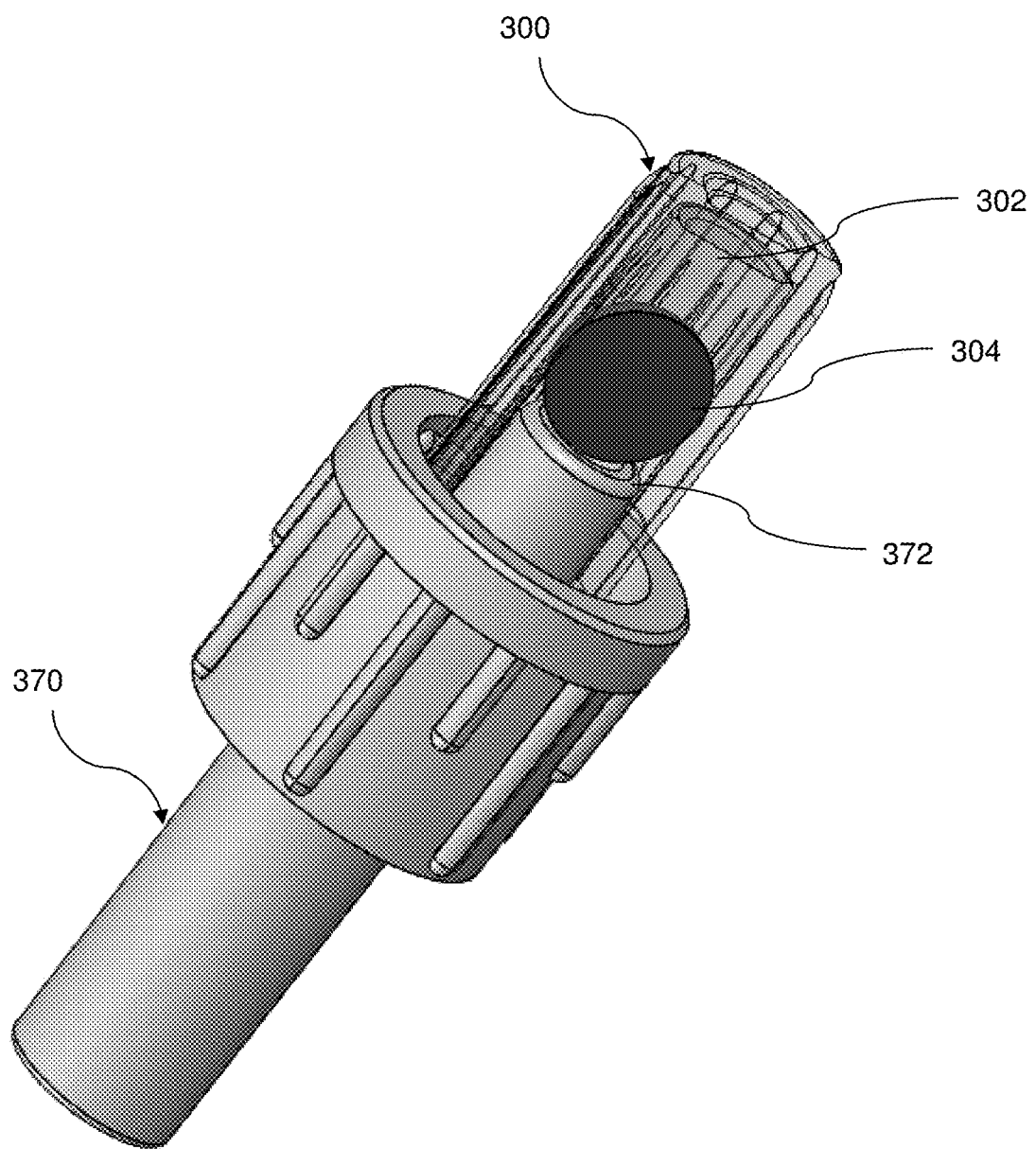
FIG. 11A illustrates a perspective view of the cap according to an exemplary third embodiment of the disclosure.
Figure 11B:
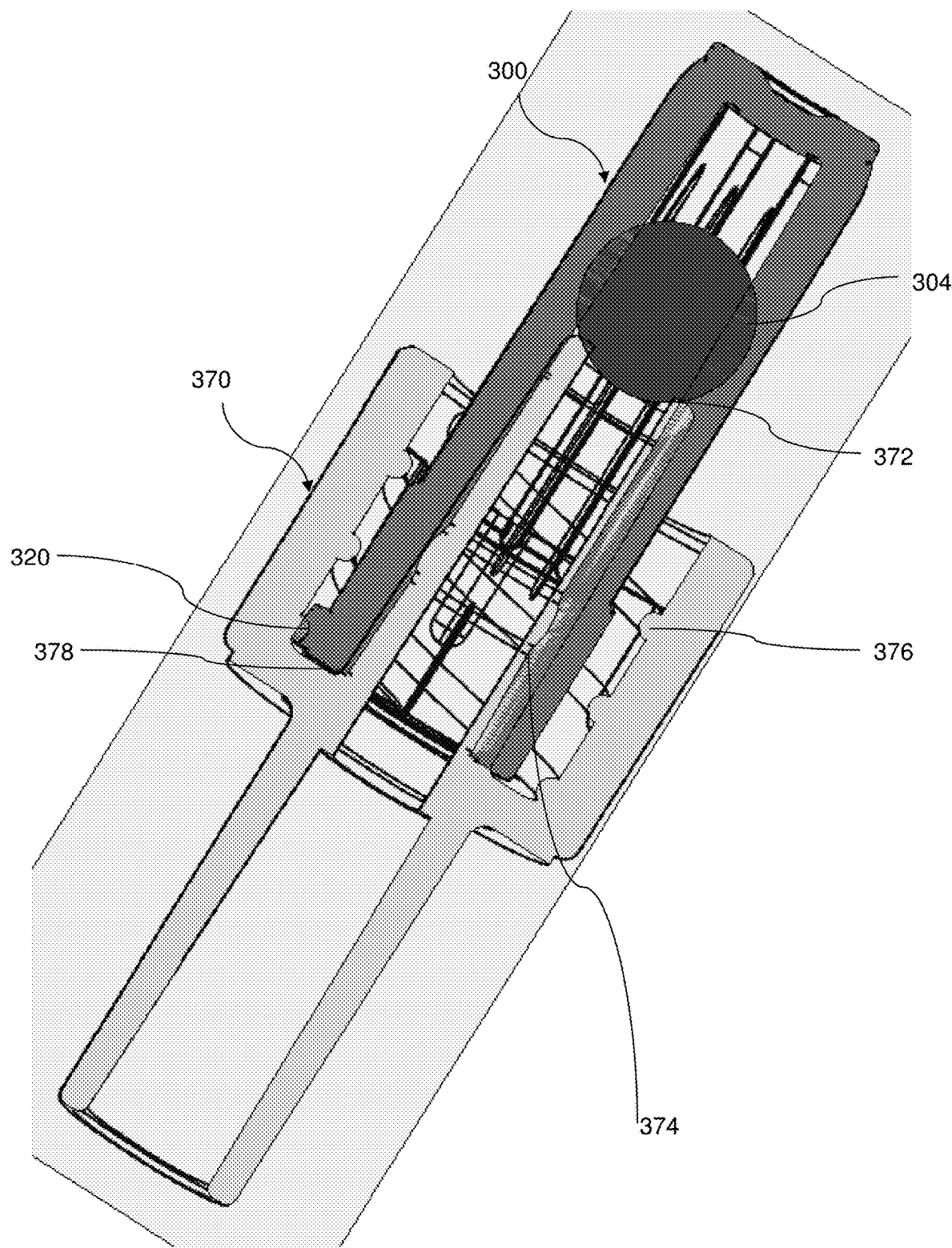
FIG. 11B illustrates a perspective cross-sectional view of the cap according to an exemplary third embodiment of the disclosure.

As shown in FIGS. 10A and 10B, an exemplary threaded male fitting 370 is depicted. The threaded male fitting 370 includes a lumen 372 disposed through a conical surface 374, a mating feature having at least one thread 376, and a mating surface 378 disposed at the bottom of the conical surface 374. FIGS. 11A and 11B illustrate the ball 304 compressed into the cap 300 by having engaged the thread 320 of the cap 300 onto the corresponding at least one thread 376 of the threaded male fitting 370. The surface of the rim 324 of the cap 300 abuts the mating surface 378 of the threaded male fitting 370. The ball 304 seals the lumen 372, preventing disinfectant from entering a flow path of the threaded male fitting 370.

Figure 14:
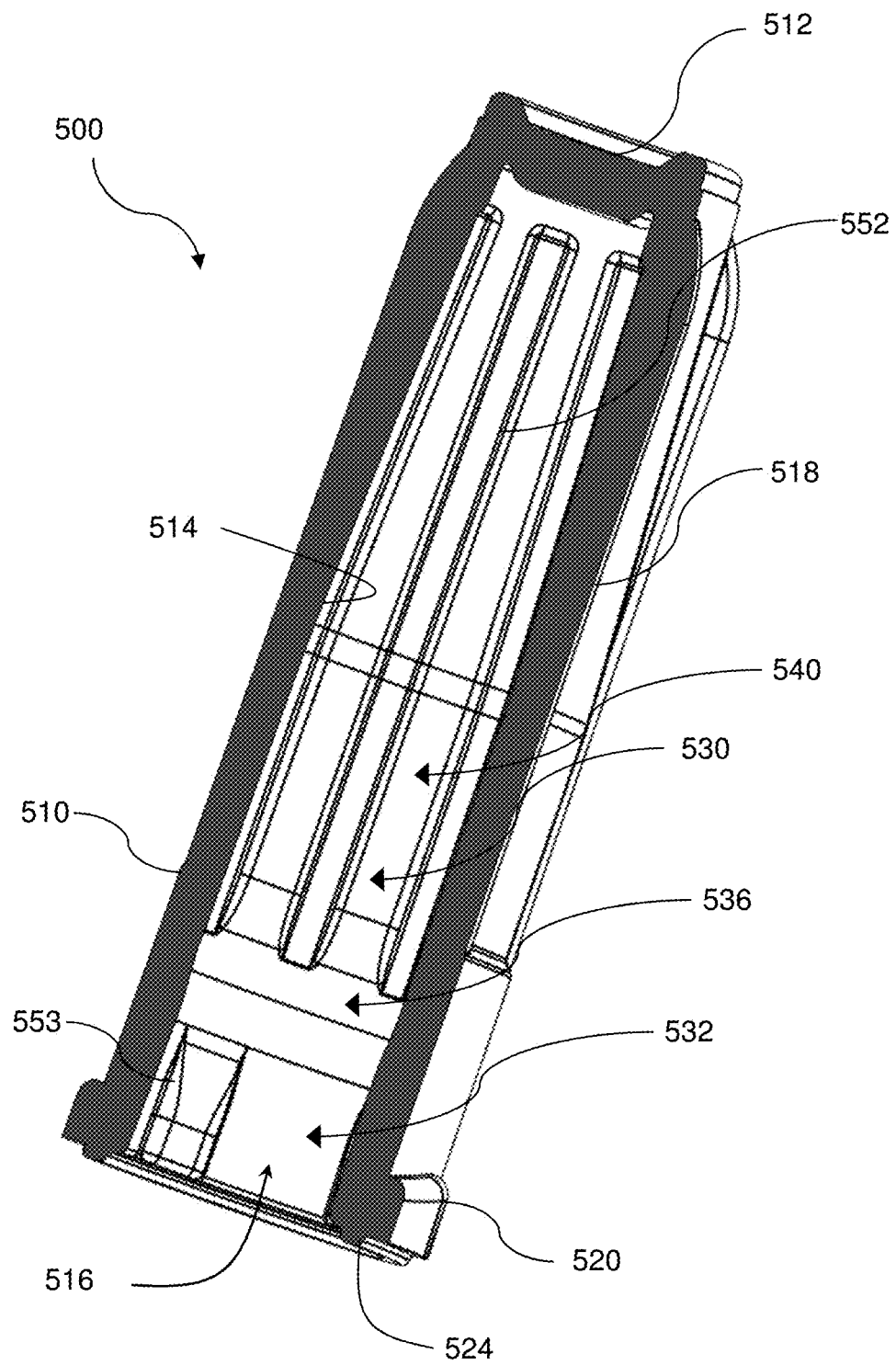
FIG. 14 illustrates a cross-sectional view of the cap according to an exemplary fifth embodiment of the disclosure.

In one or more embodiments of an exemplary cap 500, as shown in FIG. 14, a housing 510 comprises a top wall 512, an essentially cylindrical sidewall 514 forming a cavity 530, and an open bottom 516 formed by the cylindrical sidewall with an opening to the cavity 530 within the housing 510 for receiving a hub of a connector of a medical device. A thread 520 is disposed on the outer surface 518 of the housing 510, the thread 520 being configured to interlock with a mating feature of the male luer connector. In one or more embodiments, the thread 520 may be formed as at least two tabs which may interlock with a twist-to-lock mating feature of the connector of the medical device. In further embodiments, the thread may be inclined or helical in shape, corresponding with the mating feature of the connector of the medical device intended to be sterilized. The essentially cylindrical sidewall 514 further comprises a rim 524. The rim 524 protrudes from the open bottom 516 in a proximal direction. The rim 524 is configured to prevent excess disinfectant from spilling into a periphery of a luer connector upon full insertion of the cap 500.

The cylindrical sidewall 514 includes a first cylindrical portion 532, an indented portion 536 and a second cylindrical portion 540. A proximal end of the first cylindrical portion 532 is situated adjacent to the open bottom 516. A distal end of the first cylindrical portion is disposed adjacent to a proximal end of the indented portion 536. A proximal end of the second cylindrical portion 540 is disposed adjacent to a distal end of the indented portion 536. In some embodiments, chamfered or rounded transitions may be disposed at the transitions from the first cylindrical portion 532 to the indented portion 536, and from the indented portion 538 to the second cylindrical portion 540.

The proximal section 548 of the second cylindrical portion 540 further includes a plurality of top flow channels 552 in which fluid flows through as a ball is pushed within the proximal section 548, as described in embodiments of the present invention. The plurality of top flow channels 552 extend radially into the housing 510. The plurality of top flow channels 552 extend from the distal chamfer 546 to the distal section 550, the proximal and distal ends of the plurality of top flow channels 552 being tapered. In one or more embodiments, the plurality of top flow channels 552 have a substantially rectangular cross-sectional shape.

Figure 15:
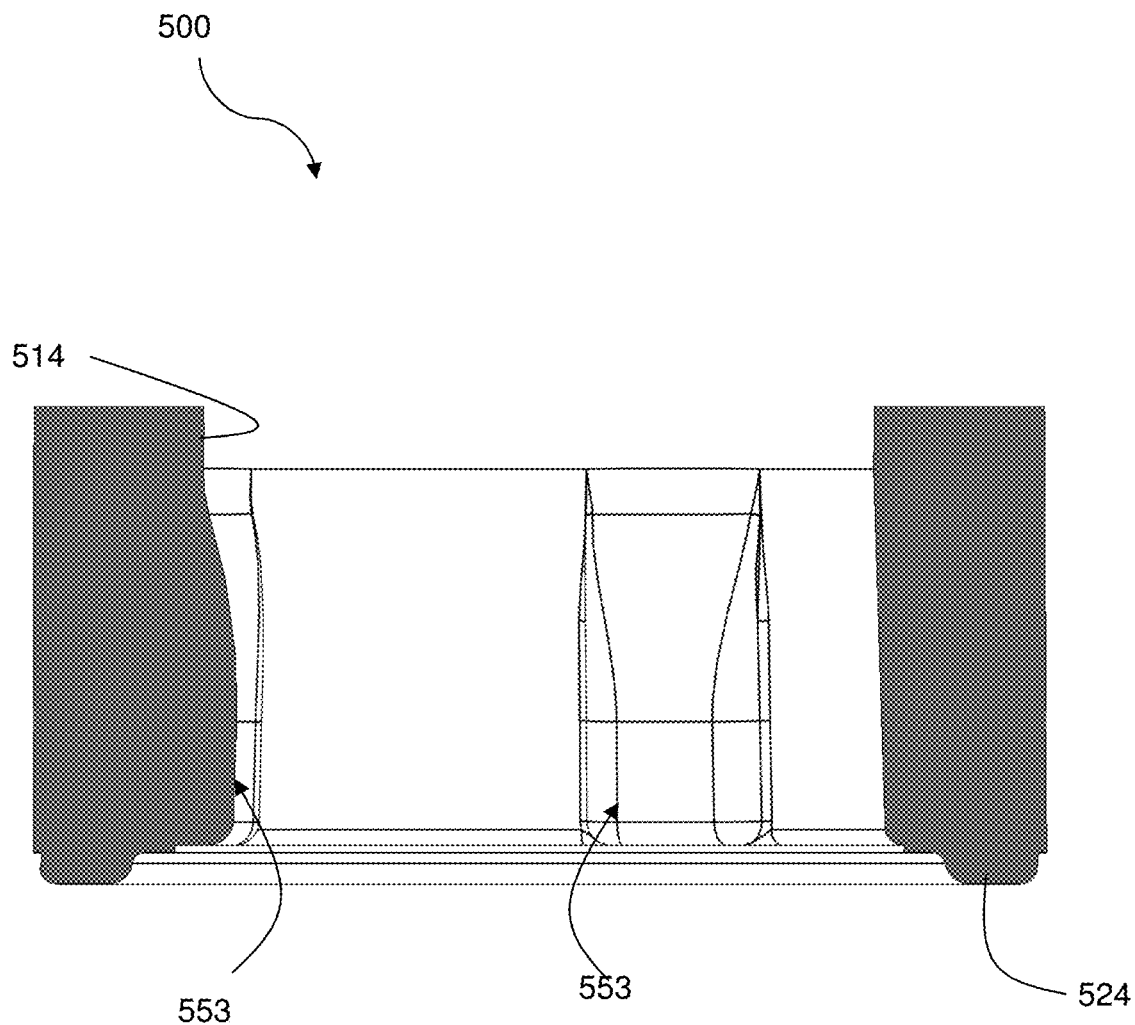
FIG. 15 illustrates a perspective view of the cap according to the exemplary fifth embodiment of the disclosure.

In one or more embodiments, the first cylindrical portion 532 may further include a plurality of tabs 553 configured to have an interference fit with a hub of a male luer connector. The shape of the plurality of tabs 553 is sized to create sufficient resistance with the hub the male luer connector to prevent accidental or unintended removal of the cap 500 from the male luer connector. As shown in FIGS. 14 through 15, in one or more embodiments, the plurality of tabs 553 have a trapezoidal cross-sectional shape, wherein a proximal end of the trapezoidal cross-sectional shape is at a substantially right angle with the cylindrical sidewall 514. In one or more embodiments, a distal end of the trapezoidal cross-sectional shape tapers in a distal direction from the proximal end of the trapezoidal cross-sectional shape. In one or more embodiments, where the sidewall has a loose fit with the hub of the male luer connector, the cap 500 is secured by the interference fit of the plurality of tabs 553.

Figure 16:
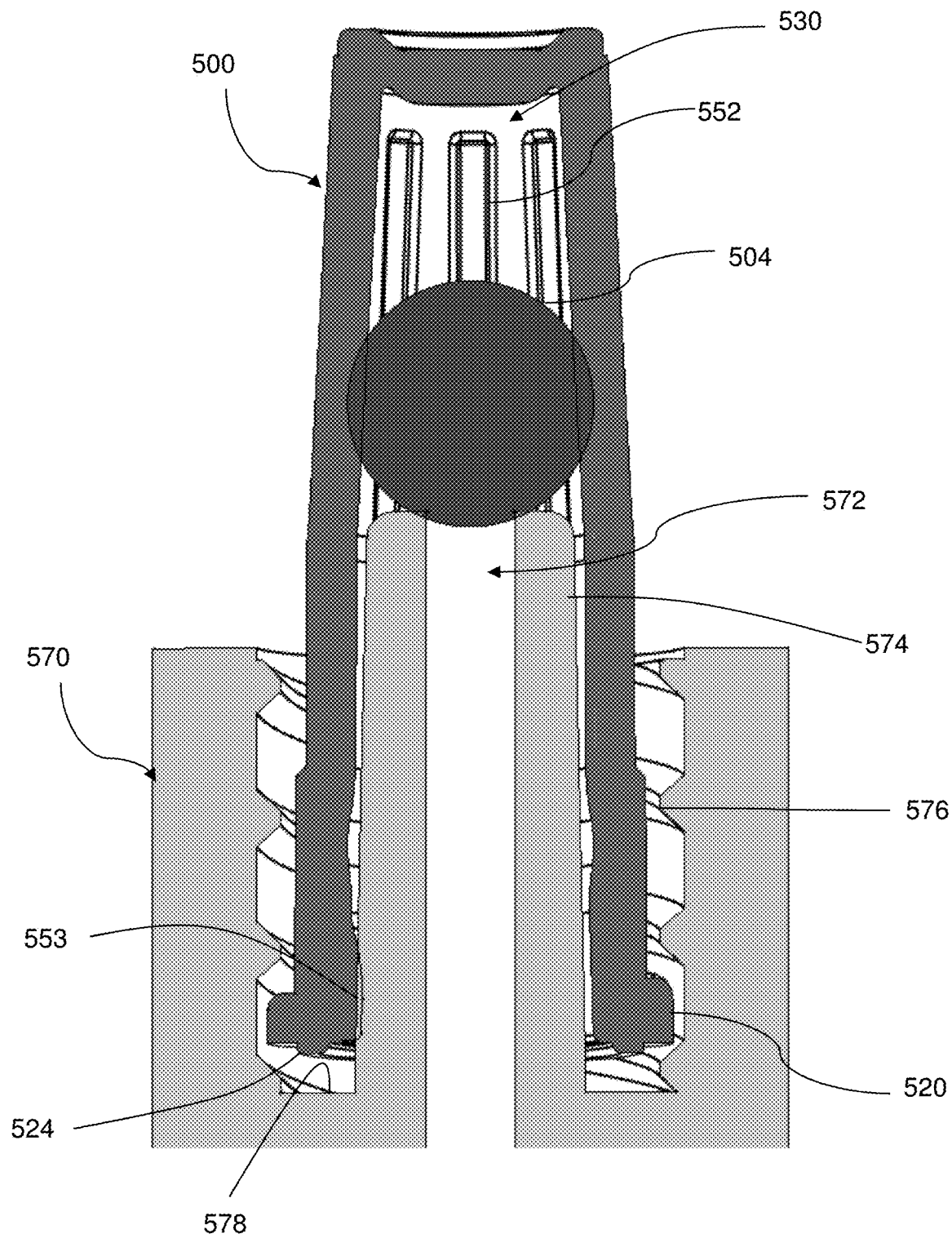
FIG. 16 illustrates a cross-sectional view of the cap according to an exemplary sixth embodiment of the disclosure.

As shown in FIG. 16, an exemplary threaded male fitting 570 is depicted. The threaded male fitting 570 includes a lumen 572 disposed through a distal tip 574 having a conical surface, a mating feature having at least one thread 576, and a mating surface 578 disposed at the proximal end of the distal tip 574. A ball 504 is compressed into the cap 500 by having engaged the thread 520 of the cap 500 onto the corresponding at least one thread 576 of the threaded male fitting 570. In one or more embodiments, the surface of the rim 524 of the cap 500 may abut the mating surface 578 of the threaded male fitting 570, thereby preventing excess disinfectant from escaping. As previously described in embodiments of the present invention, the ball 504 seals the lumen 572, preventing disinfectant from entering a flow path of the threaded male fitting 570, the disinfectant being stored within the cavity 530 behind the ball 504. The disinfectant disinfects the conical surface of the hub 574 and the periphery of the threaded male fitting. The plurality of tapered tabs 553 form a drafted sidewall surface configured to have an interference fit with a hub of a male luer connector. In one or more embodiments, the plurality of tapered tabs 553 are disposed on the inner surface of the sidewall at the open end of the cap to form a longitudinal draft configured to have an interference fit with a hub of a male luer connector.

Figure 17:
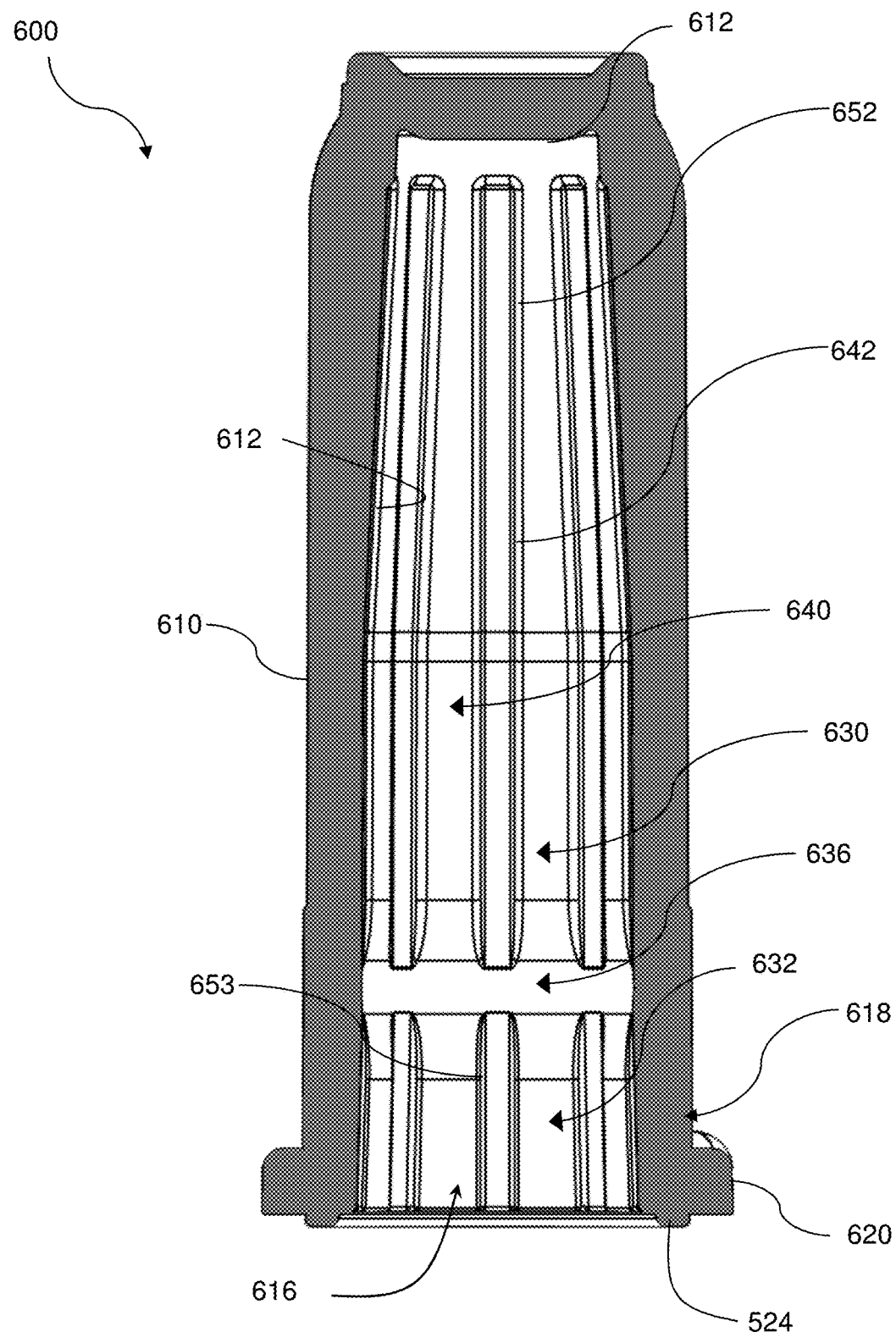
FIG. 17 illustrates a perspective view of the cap according to the exemplary sixth embodiment of the disclosure.

In one or more embodiments of an exemplary cap 600, as shown in FIG. 17, a housing 610 comprises a top wall 612, an essentially cylindrical sidewall 614 forming a cavity 630, and an open bottom 616 formed by the cylindrical sidewall with an opening to the cavity 630 within the housing 610 for receiving a hub of a connector of a medical device. A thread 620 is disposed on the outer surface 618 of the housing 610, the thread 620 being configured to interlock with a mating feature of the male luer connector. In one or more embodiments, the thread 620 may be formed as at least two tabs which may interlock with a twist-to-lock mating feature of the connector of the medical device. In further embodiments, the thread may be inclined or helical in shape, corresponding with the mating feature of the connector of the medical device intended to be sterilized The essentially cylindrical sidewall 614 further comprises a rim 624. The rim 624 protrudes from the open bottom 616 in a proximal direction. The rim 624 is configured to prevent excess disinfectant from spilling into a periphery of a luer connector upon full insertion of the cap 600.

The cylindrical sidewall 614 includes a first cylindrical portion 632, an indented portion 636 and a second cylindrical portion 640. A proximal end of the first cylindrical portion 632 is situated adjacent to the open bottom 616. A distal end of the first cylindrical portion is disposed adjacent to a proximal end of the indented portion 636. A proximal end of the second cylindrical portion 640 is disposed adjacent to a distal end of the indented portion 636. In some embodiments, chamfered or rounded transitions may be disposed at the transitions from the first cylindrical portion 632 to the indented portion 636, and from the indented portion 638 to the second cylindrical portion 640.

The proximal section 648 of the second cylindrical portion 640 further includes a plurality of top flow channels 652 in which fluid flows through as a ball is pushed within the proximal section 648, as described in embodiments of the present invention. The plurality of top flow channels 652 extend radially into the housing 610. The plurality of top flow channels 652 extend from the distal chamfer 646 to the distal section 650, the proximal and distal ends of the plurality of top flow channels 652 being tapered. In one or more embodiments, the plurality of top flow channels 652 have a substantially rectangular cross-sectional shape.

In one or more embodiments, the first cylindrical portion 632 may further include a plurality of bottom flow channels 652 in which fluid flows through as the ball is pushed within the proximal section 648 of the second cylindrical portion 640. When the ball sits within the indented portion 636, fluid or gas cannot flow from the plurality of top flow channels 642 to the plurality of bottom flow channels 644, as the ball is in an interference fit with the indented portion 636. The plurality of bottom flow channels 644 is intended to promote disinfectant or antimicrobial agent permeation towards the mating surface of the male luer connector. Compression of the ball toward the top wall 612 of housing 610 upon connection to the male luer connector allows the connector to contact the disinfectant or antimicrobial agent to disinfect the male luer connector. In one or more embodiments, the top flow channels 642 and bottom flow channels 644 have the same cross-sectional shape and width.

Figure 18:
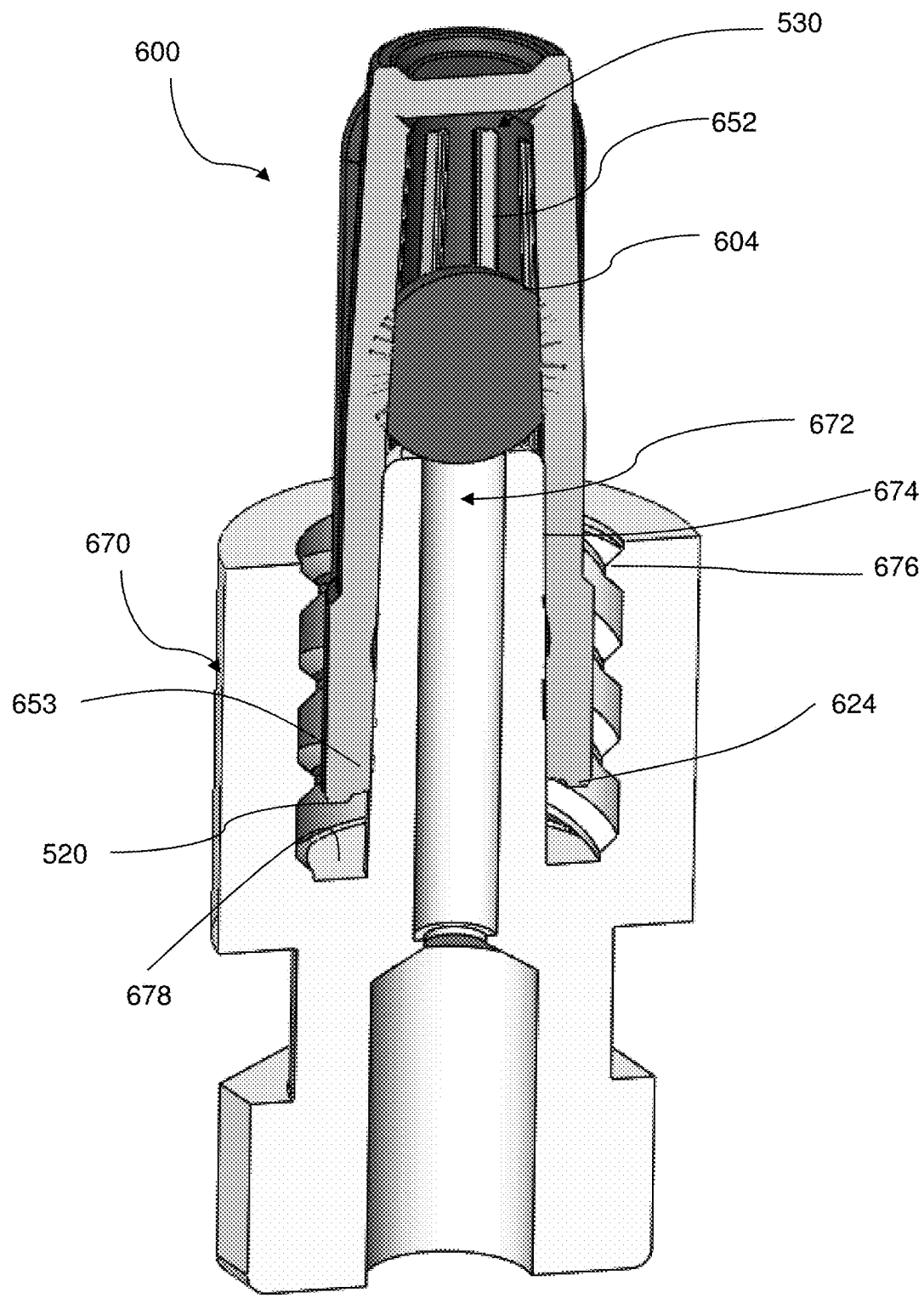
FIG. 18 illustrates a perspective view of the cap according to the exemplary sixth embodiment of the disclosure; and, FIG. 19 illustrates a perspective view of a cap according to an exemplary seventh embodiment of the disclosure.
Figure 19:
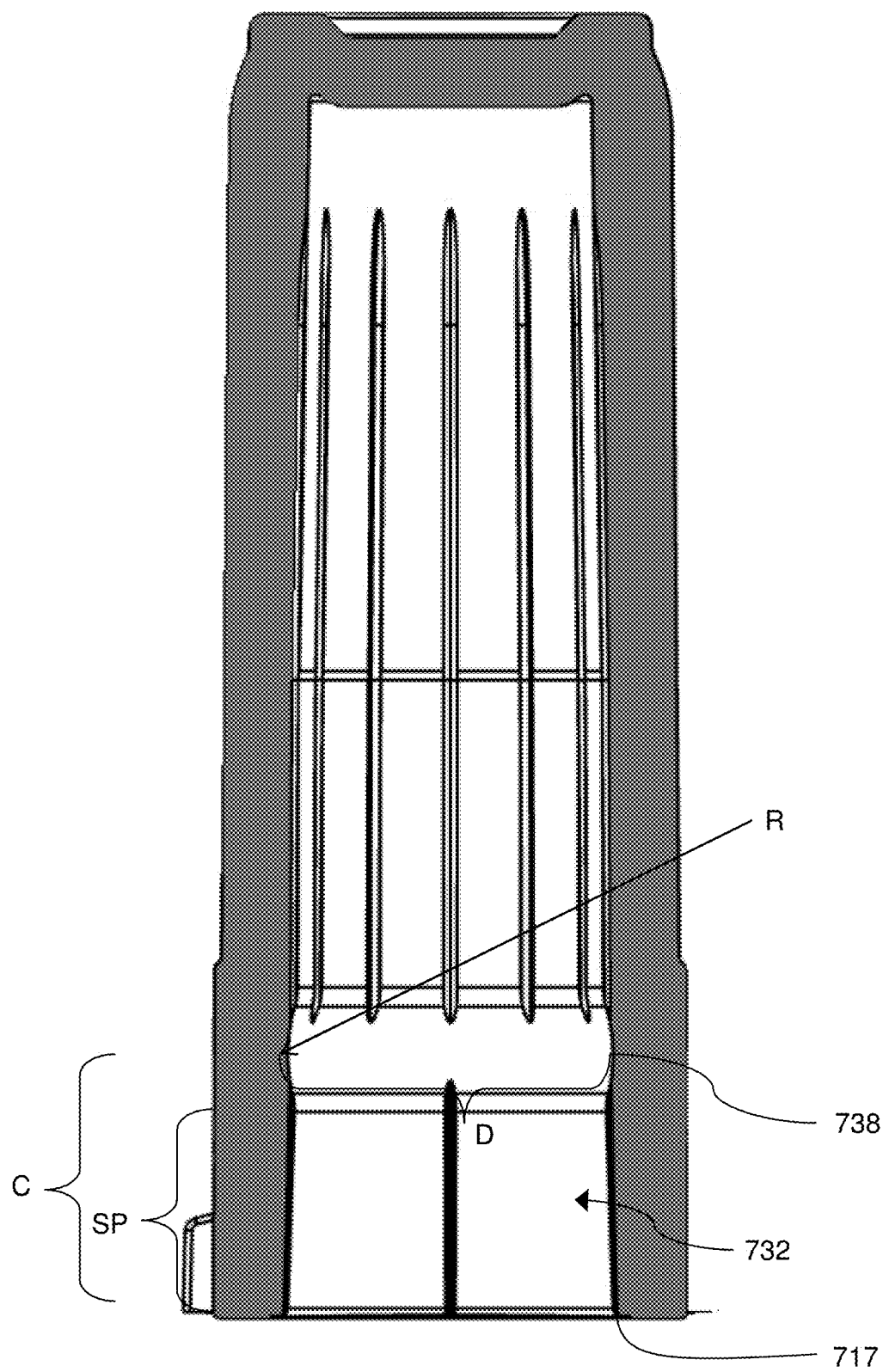

As shown in FIG. 18, an exemplary threaded male fitting 670 is depicted. The threaded male fitting 670 includes a lumen 672 disposed through a hub 674 having a conical surface, a mating feature having at least one thread 676, and a mating surface 678 disposed at the proximal end of the hub 674. A ball 604 is compressed into the cap 600 by having engaged the thread 620 of the cap 600 onto the corresponding at least one thread 676 of the threaded male fitting 670. In one or more embodiments, the surface of the rim 624 of the cap 600 may abut the mating surface 678 of the threaded male fitting 670, thereby preventing excess disinfectant from escaping. As previously described in embodiments of the present invention, the ball 604 seals the lumen 672, preventing disinfectant from entering a flow path of the threaded male fitting 670, the disinfectant being stored within the cavity 630 behind the ball 604. The disinfectant disinfects the conical surface of the hub 674 and the periphery of the threaded male fitting. The inside surface of the open bottom 616 includes a drafted sidewall surface configured to have an interference fit with a hub of a male luer connector. In one or more embodiments, the drafted sidewall surface are radially tapered outward toward the center axis of the cavity to form a longitudinal draft configured to have an interference fit with a hub of a male luer connector.

In one or more embodiments, an open bottom 716 formed by a cylindrical sidewall with an opening to a cavity within the housing for receiving a hub of a connector of a medical device has a taper 717 which tapers outwardly from the cylindrical sidewall towards the opening to the cavity. In one or more embodiments, the taper 717 is located between 0.2 mm to 1 mm from the open bottom.

In one or more embodiments, an indented portion 738 positioned adjacent to a proximal cylindrical portion 732 is defined by an arc 738. The arc 378 has an arc angle R between 3 degrees and 5 degrees and a center C of the arc angle is positioned between 3.5 mm and 4.5 mm from the opening to the cavity. The arc has a proximal starting position 387a and a distal ending position. At the proximal starting position 378a, a diameter D of the cavity is between 4.5 mm and 5 mm.

Figure 12A:
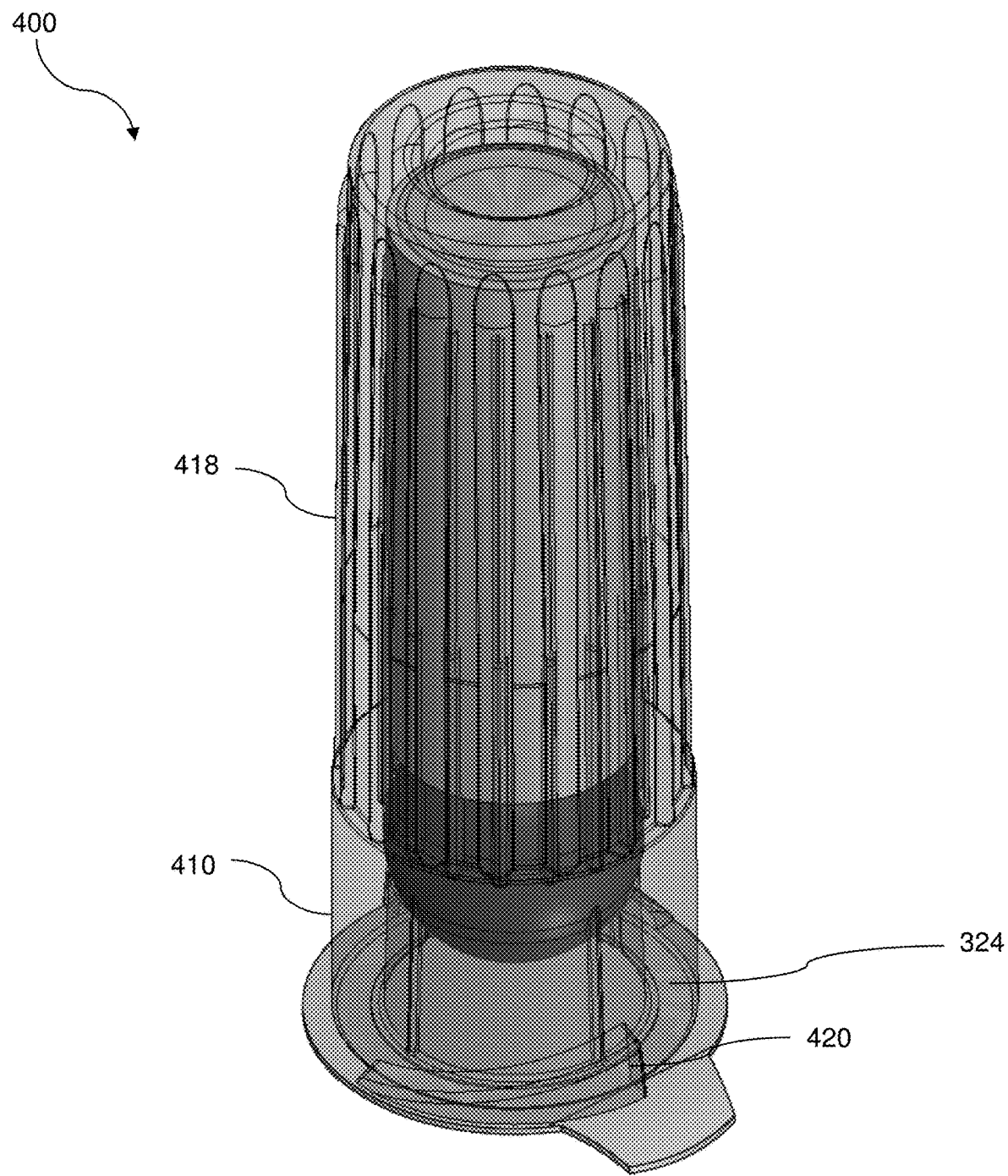
FIG. 12A illustrates a perspective view of the cap according to an exemplary fourth embodiment of the disclosure.
Figure 12B:
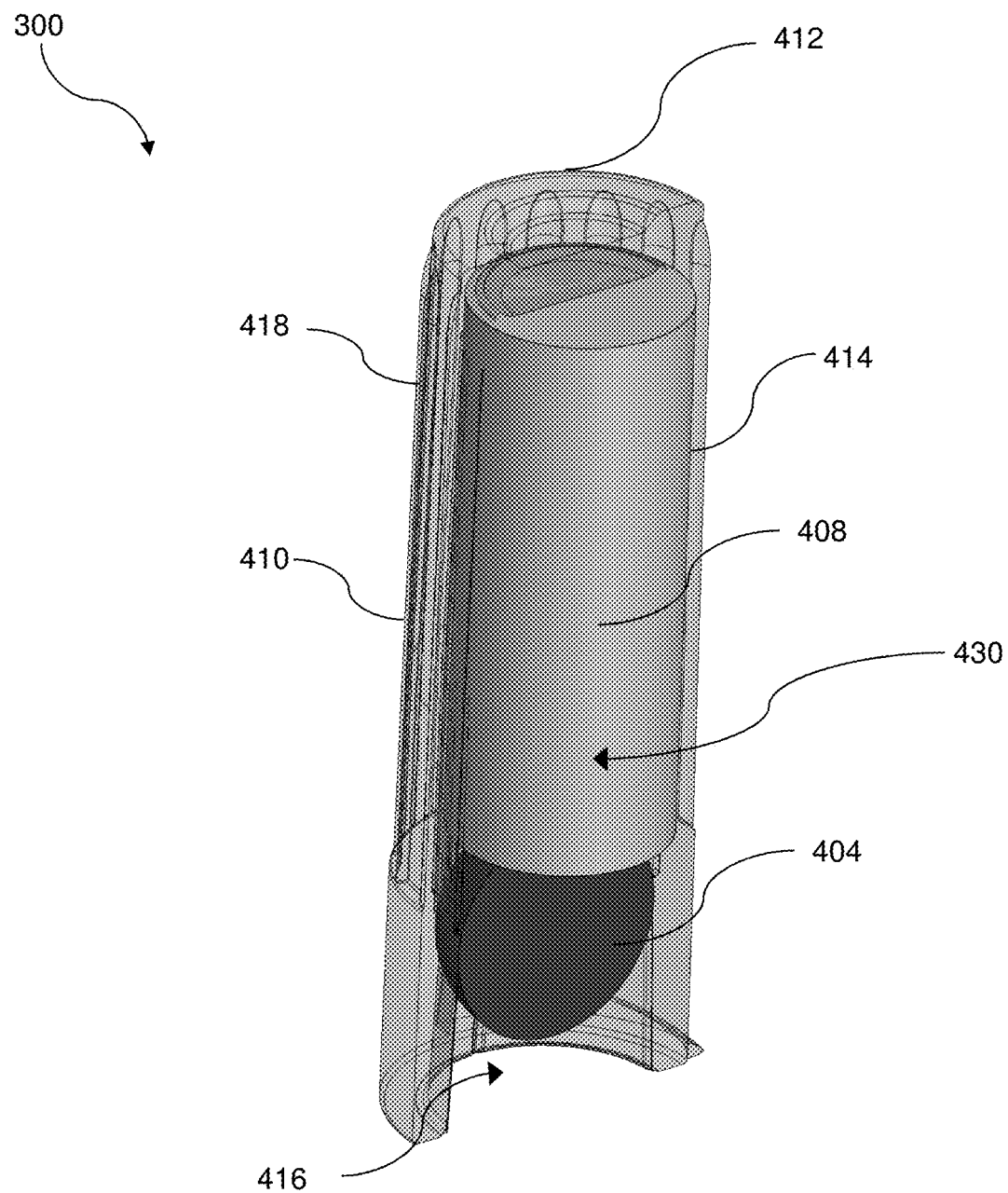
FIG. 12B illustrates a perspective cross-sectional view of the cap according to an exemplary fourth embodiment of the disclosure.

Referring to FIGS. 1-16, in one or more embodiments, the exterior surface of sidewall (114, 214, 314, 514, 614) comprises a plurality of grip members (113, 213, 313). In one or more embodiments, the plurality of grip members (113, 213, 313) are in the form of elongate ribs. A fourth aspect of the present disclosure, as shown in FIGS. 12A and 12B, pertains to a relates to a sterile cap 400, a housing 410 comprises a top wall 412, an essentially cylindrical sidewall 414 forming a cavity 430, and an open bottom 416 formed by the cylindrical sidewall 404 with an opening to the cavity 430 within the housing 410 for receiving a hub of a connector of a medical device. The connector of the medical device may be a threaded connection, a needleless connection, or in the preferred embodiment, a male luer connector. In one or more embodiments, the cavity includes a closed distal end comprising a distal wall, an open proximal end, and a sidewall extending proximally from the distal wall toward the open proximal end. In one or more embodiments, a thread 420 is disposed on the outer surface 418 of the housing 410, the thread 420 being sufficient to interlock with a mating feature of the male luer connector. In one or more embodiments, the thread may be formed as at least two tabs which may interlock with a twist-to-lock mating feature of the connector of the medical device. In further embodiments, the thread may be inclined or helical in shape, corresponding with the mating feature of the connector of the medical device intended to be sterilized. Referring to FIGS. 12A-12B, in one or more embodiments, cap 400 includes an absorbent material 408 disposed within the cavity behind the ball 404. In one or more embodiments, the disinfectant or antimicrobial agent in the cavity 430 of the cap 400 is stored by the absorbent material 408 with the ball 404 over the absorbent material 408 for sealing. In one or more embodiments, the disinfectant or antimicrobial agent disinfects an outer surface and an inner surface of the male luer connector when the male luer connector is inserted into the cavity and compresses the ball and the absorbent material 408 disposed behind the ball 404. In one or more embodiments, the absorbent material 408 is a nonwoven material, foam or a sponge. In one or more embodiments, the absorbent material is an open-cell sponge. In a specific embodiment, the foam is a polyurethane foam. In one or more embodiments, the absorbent material is retained in the chamber by an interference fit with the inner sidewall of the chamber. When the cap 400 is attached to a luer device, the male luer pushes against the ball 404 to displace the ball 404 toward closed end of the cap housing, with the ball 404 compressing the absorbent material 408 to release disinfectant onto luer surface.

In one or more embodiments, a compression of the absorbent material toward the top wall of the housing occurs upon connection of the disinfection cap to a luer connector, whereby compression of the absorbent material leads to the leakage of the disinfectant or antimicrobial agent within the cavity to disinfect the luer connector. The cap (100, 200, 300, 400, 500, 600) can achieve disinfection when used on luer connectors by integrating disinfectant or antimicrobial agent in the cavity (130, 230, 330, 530, 630) of the cap (100, 200, 300, 500, 600). The disinfectant or antimicrobial agent (102, 202, 302) can be directly included in the cavity (130, 230, 330, 530, 630). Cap (100, 200, 300, 500, 600) is designed to be compatible in interacting with various disinfectant or antimicrobial agent (102, 202, 302). In one or more embodiments, the disinfectant or antimicrobial agent (102, 202, 302) may include variations of alcohol or chlorhexidine. In one or more embodiments, the disinfectant or antimicrobial agent (102, 202, 302) may include variations of alcohol or chlorhexidine. In one or more embodiments, the disinfectant or antimicrobial agent (102, 202, 302) is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent (102, 202, 302) is a fluid or a gel.

In one or more embodiments, the cap (100, 200, 300, 500, 600) can include a removable peel seal (122, 222, 322) covering the opening to the cavity (130, 230, 330) to seal the ball (104, 204, 304, 504, 604) and disinfectant or antimicrobial agent (102, 202, 302) within the cavity (130, 230, 330, 530, 630) prior to use of the cap (100, 200, 300, 500, 600). In one or more embodiments, the peelable seal (122, 222, 322) comprises an aluminum or multi-layer polymer film peel back top. In a specific embodiment, the peelable seal (122, 222, 322) is heat-sealed or induction sealed to the open end of the cap (100, 200, 300). In one or more embodiments, the peelable seal (122, 222, 322) comprises a moisture barrier.

In the preferred embodiment the ball (104, 204, 304, 504, 604) can be compressible and may be a thermoplastic elastomer ("TPE"), thermoplastic olefin ("TPO"), or an elastomer or deformable material. In other embodiments, the ball (104, 204, 304, 504, 604) may be of a rigid or hard plastic causing the housing (110, 210, 310) to deform. In further embodiments, the ball (104, 204, 304, 504, 604) may be glass, ceramic, metal or a composite material.

In one or more embodiments, the disinfectant or antimicrobial agent (102, 202, 302) disinfects an outer surface or periphery of the male luer connector when the male luer connector is inserted into the cavity (130, 230, 330, 530, 630) and pushes the ball in a distal direction. In the preferred embodiment, the insertion compresses the ball (104, 204, 304, 504, 604). The ball (104, 204, 304, 504, 604) forms an interference fit with an inner wall of the cavity (130, 230, 330, 530, 630) of the cap (100, 200, 300, 500, 600). In one or more embodiments, the ball (104, 204, 304, 504, 604) is soft and can form slight clearance with inner sidewall of the cavity (130, 230, 330, 530, 630) when subject to pressure.

The cap (100, 200, 300, 500, 600) is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap (100, 200, 300, 500, 600) comprises a polypropylene or polyethylene material.

In one or more embodiments, the connector of the medical device may be selected from the group consisting essentially of needle-free connectors, catheter luer connectors, stopcocks, and hemodialysis connectors on primary IV gravity sets, secondary IV gravity sets, extension sets, and infusion or syringe pump sets. In some embodiments, the cap can be connected with any of a variety of different needleless injection sites. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap (100, 200, 300, 500, 600) replaces the standard swabbing protocol for cleaning connectors.

A fifth aspect of the present disclosure pertains to a method of disinfecting a medical connector. The method comprises connecting the cap (100, 200, 300, 500, 600) of one or more embodiments to a medical connector, wherein connecting includes engaging the threads of the medical connector onto the threads (120, 220, 320, 520, 620) on the outer surface of the sidewall (114, 214, 314, 514, 614) of the housing (110, 210, 310, 510, 610) of the cap upon insertion of the medical connector into the cap (100, 200, 300, 500, 600) such that the medical connector contacts the ball (104, 204, 304, 504, 604) and the disinfectant or antimicrobial agent (102, 202, 302).

A sixth aspect of the present disclosure pertains to an assembly. The assembly comprises the cap (100, 200, 300, 500, 600) of one or more embodiments connected to a medical connector. In one or more embodiments, the medical connector is selected from a male luer connector, or other needleless connector having a male fitting. In one or more embodiments, the male connector may be selected from the group consisting essentially of needle-free connectors, catheter luer connectors, stopcocks, and hemodialysis connectors.

Figure 13:
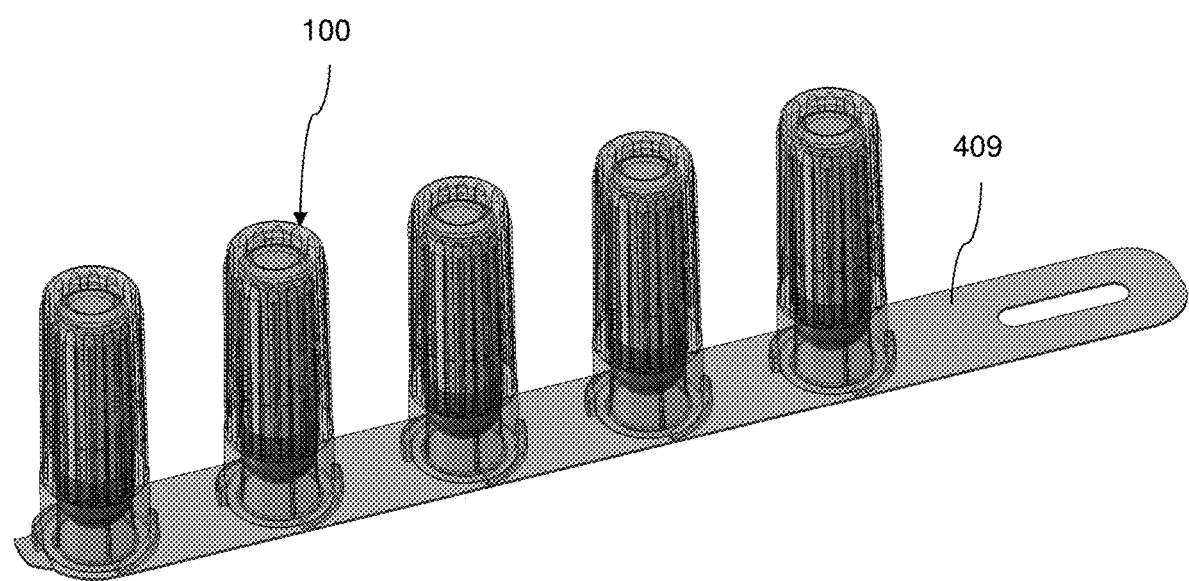
FIG. 13 illustrates a detailed perspective view of packaging of a connector cap according to an exemplary embodiment of the disclosure.

A seventh aspect of the present disclosure pertains to packaging. Referring to FIG. 13, in one or more embodiments, cap (100, 200, 300, 400, 500, 600) can be packaged into a strip configuration. As shown in FIG. 13, the strip configuration may comprise a single-piece top web 409 on which multiple caps (100, 200, 300, 400, 500, 600) are attached through a sealing layer. The strip configuration may also comprise individually sealed caps with individual top web foil, and then a series of individually sealed caps are attached to a piece of strip composed of materials such as plastic in an arrayed fashion. The individual top web foil can have a tab that is attached to the strip material through adhesive or through sealant.

It is contemplated that the disinfection cap (100, 200, 300, 400, 500, 600) disclosed herein and shown in the Figures may also be utilized with female connectors, including female luer connectors, wherein ball (104, 204 304, 404, 504, 604) can be used to block the lumen of open female luers to facilitate the mitigation of such disinfectant ingress into connectors, thereby reducing risk of the disinfectant entering the blood stream. It is therefore contemplated that the disinfection cap (100, 200, 300, 500, 600) disclosed herein and shown in the Figures may be utilized with both male and female connectors.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cap comprising:
    a housing comprising
      a top wall,
      an essentially cylindrical sidewall forming a cavity,
      one or more ribs disposed on an inner surface of the cavity;
    a ball disposed within the cavity;
    a disinfectant or an antimicrobial agent;
    an open bottom formed by said cylindrical sidewall with an opening to the cavity within said housing for receiving a hub of a male luer connector; and
    an outer thread on said outer surface of the cylindrical sidewall, said outer thread being sufficient to interlock with a mating feature of said male luer connector;
    the cavity having an inner surface having a first portion adjacent to the open bottom having a straight cylindrical sidewall having a first diameter D1 which is smaller than the diameter of the ball, a second tapered portion disposed adjacent to the first portion wherein the second tapered portion having a second diameter D2 that increases along the y-axis in a direction from the open bottom toward a top wall of the cavity, and a third portion having a straight cylindrical sidewall having the one or more ribs protruding toward a central axis of the cavity, the third portion of the inner surface of the cavity disposed adjacent to the second portion and having a diameter D3 that is equal to or greater than the diameter of the ball.

2. The cap of claim 1, wherein when the hub of said male luer connector is received within said inner surface of said cavity, said hub of said male luer connector is secured within said inner surface of said cavity by interlocking at least a portion of said outer thread with a mating feature on said hub of said male luer connector.

3. The cap of claim 1, further comprising a removable seal or septum attached to the open bottom forming a seal for maintaining said disinfectant or said antimicrobial agent within said cavity prior to use of said cap.

4. The cap of claim 1, wherein an exterior wall surface of the sidewall includes a plurality of grip members.

5. The cap of claim 1, wherein a compression of the ball toward the top wall of the housing occurs upon connection to the male luer connector.

6. The cap of claim 5, wherein compression of the ball disinfects the male luer connector.

7. The cap of claim 1, wherein the ball is under radial compression by a ringed indent on said inner surface of the cavity to retain the ball in the cavity.

8. The cap of claim 1, wherein the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

9. The cap of claim 8, wherein the disinfectant or antimicrobial agent comprises at least one of chlorhexidine gluconate and chlorhexidine diacetate.

10. A cap comprising:
    a housing comprising
      a top wall,
      an essentially cylindrical sidewall forming a cavity, the cavity having an inner surface;
    a ball disposed within an indented portion of the cavity, the indented portion positioned adjacent to a second portion of the cavity, the indented portion and the ball forming a liquid seal;
    a plurality of top channels disposed on a surface of the second portion of the cavity, the second portion having a diameter D1, the diameter D1 being larger than a diameter of the ball;

a disinfectant or antimicrobial agent disposed within the second portion of the cavity;

an open bottom formed by said cylindrical sidewall with an opening to the cavity within said housing for receiving a hub of a male luer connector; and, the inner surface of the cavity having a first portion adjacent to the open bottom having a tapered sidewall, the first portion having a second diameter D2 which is smaller than the diameter of the ball, the second diameter D2 increasing along the y-axis in a direction from the open bottom toward a top wall of the cavity.

11. The cap of claim 10, wherein an outer thread on an outer surface of the cylindrical sidewall, said outer thread being sufficient to interlock with a mating feature of said male luer connector.

12. The cap of claim 10, wherein the first portion includes a plurality of tabs configured to have an interference fit with the hub of the male luer connector.

13. The cap of claim 10, wherein a plurality of lower channels are disposed on the first portion.

14. The cap of claim 10, further comprising a removable seal or septum attached to the open bottom of the cavity forming a seal for maintaining said disinfectant or an antimicrobial agent within said cavity prior to use of said cap.

15. The cap of claim 10, wherein an exterior wall surface of the sidewall includes a plurality of grip members.

16. The cap of claim 10, wherein a compression of the ball toward the top wall of the housing occurs upon connection to the male luer connector.

17. The cap of claim 10, wherein compression of the ball disinfects the male luer connector.

18. The cap of claim 10, wherein the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

19. The cap of claim 18, wherein the disinfectant or antimicrobial agent comprises at least one of chlorhexidine gluconate and chlorhexidine diacetate.

* * * * *